United States Patent [19]

Isomura et al.

[11] Patent Number: 5,480,875
[45] Date of Patent: Jan. 2, 1996

[54] CRYSTAL OF MONOHYDRATE OF HETEROCYCLIC BIS(PHOSPHONIC ACID) DERIVATIVE

[75] Inventors: Yasuo Isomura; Makoto Takeuchi, both of Ibaraki; Mamoru Hamada; Yoshisaburo Kaneko, both of Saitama; Noriya Yamamoto, Ibaraki, all of Japan

[73] Assignee: Yamanouchi Pharmaceutical Co., Ltd., Tokyo, Japan

[21] Appl. No.: 360,701

[22] PCT Filed: Jun. 18, 1993

[86] PCT No.: PCT/JP93/00821

§ 371 Date: Dec. 21, 1994

§ 102(e) Date: Dec. 21, 1994

[87] PCT Pub. No.: WO94/00462

PCT Pub. Date: Jan. 6, 1994

[30] Foreign Application Priority Data

Jun. 23, 1992 [JP] Japan ...................... 4-205872

[51] Int. Cl.[6] ................................. C07D 471/04
[52] U.S. Cl. ................................. 514/80; 546/23
[58] Field of Search ................... 546/23; 514/80

[56] References Cited

U.S. PATENT DOCUMENTS 4,990,503  2/1991  Isomura et al. .................... 514/80
5,039,669  8/1991  Isomura et al. .................... 514/80

FOREIGN PATENT DOCUMENTS 354806   of 1989  European Pat. Off. .
0354806  2/1990   European Pat. Off. .

*Primary Examiner*—C. Warren Ivy
*Assistant Examiner*—Amelia Owens
*Attorney, Agent, or Firm*—Burgess, Ryan & Wayne

[57] ABSTRACT

Crystal D or E of 1-hydroxy-2-(imidazo[1,2-a]pyridin-3-yl)ethane -1,1-bis(phosphonic acid) monohydrate having specified lattice spacing and relative intensity in the powder X-ray diffraction spectrum obtained by using Cu-Kα radiation and a dehydration peak temperature of 135° to 149° C. or 160° to 170° C. according to TG-DSC thermogravimetric analysis; and to a solid pharmaceutical preparation containing the same. The crystals are useful for producing a stable solid pharmaceutical preparation of the above compound which has an excellent drug efficacy for diseases wherein increased bone resorption participates, such as osteoporosis.

9 Claims, 21 Drawing Sheets

MAGNIFICATION: 250

MAGNIFICATION: 250

MAGNIFICATION: 250

CRYSTAL OF MONOHYDRATE OF HETEROCYCLIC BIS(PHOSPHONIC ACID) DERIVATIVE

This application is a 371 of PCT/JP93/00821 filed Jun. 18, 1993.

TECHNICAL FIELD

This invention relates to novel crystals D and E of a novel monohydrate of 1-hydroxy-2-(imidazo[1,2-a]pyridin-3-yl)ethane-1,1-bis(phosphonic acid), to be referred to as compound (I) hereinafter, and to a stable solid pharmaceutical preparation containing the same.

BACKGROUND ART

Compound (I) is a compound represented by the following formula (I), which has excellent bone resorption inhibitory activity, anti-inflammatory activity and analgesic-antipyretic activity and is useful for the treatment of diseases in which increased bone resorption participates, such as Paget's disease, hypercalcemia, bone metastasis of cancer and osteoporosis, as well as progress in the bone resorption (induction of osteoporosis) caused by inflammatory joint diseases such as rheumatoid arthritis and the like (cf. JP-A-2-138288). (The term "JP-A" as used herein means an "unexamined published Japanese patent application.)

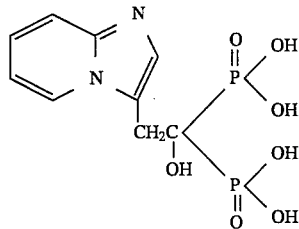

Example 5 in the aforementioned published patent application describes that this free acid compound (I) is isolated and purified in the form of colorless needle crystals which are obtained by recrystallization from water-methanol, and the thus obtained crystals contain 0.5 mole of water according to the result of elemental analysis.

However, the aforementioned published patent application does not describe about certain properties of the crystal obtained in the Example 5 which are not desirable when compound (I) is made into a pharmaceutical preparation, with respect to the presence of compound (I) monohydrate which has two novel crystalline forms and about utility of the novel monohydrate crystals.

According to the studies conducted by tile inventors of the present invention, it was confirmed that the crystalline form of the crystal produced in accordance with the procedure described in Example 5 of the aforementioned published patent application (to be referred to as crystal C hereinafter, Lot No. 49-1 in the table) was physically unstable, because it has such a strong hygroscopic property that it absorbs 1% of moisture in a day under a relative humidity condition of 93% (cf. crystal C in Table 3) and the crystalline form was changed and converted into monohydrate in the presence of water (cf. Test Example 3 which will be described later). In consequence, it was revealed that this crystal has serious problems in putting it into practical use as a solid pharmaceutical preparation because of various limitations in the preservation of the crystal and in the pharmaceutical manufacturing steps.

When the crystal C was examined in detail, it was confirmed that the crystal C was an anhydride crystal containing 0.5 mole of free water, because its thermal analysis does not show an endothermic peak due to dehydration of water of crystallization and its powder X-ray diffraction pattern did not change even after removal of the 0.5 mole equivalent water by 3 hours of drying at 150° C. In addition, though the crystal C was the same colorless needle crystal as the crystal of Example 5 of the aforementioned published patent application when observed by the naked eye, it was a lump of minute plate crystals when examined microscopically under a polarization microscope (cf. the photograph of the crystal).

In consequence, the present inventors have attempted to produce crystals of sodium salts which are commonly used to give the crystalline form of phosphoric acid compounds, but such crystals, except for monosodium salt, were not able to be produced even in an amount useful examination, because disodium salt did not crystallize and trisodium salt did not give a stable crystal.

On the contrary, the monosodium salt gave relatively stable crystals as a dihydrate (to be referred to as crystal A hereinafter, Lot No. T-8 in the table) and a trihydrate (to be referred to as crystal B hereinafter, Lot No. T-10 in the table), but each of these crystals was disadvantageously apt to release water of crystallization. It was found that these crystals release 0.5 to 1 mole equivalent amount of water of crystallization when allowed to stand at 80° C. for 5 hours and 1 to 2 mole equivalent amount of water of crystallization at 105° C. (cf. crystals A and B in Table 3).

In consequence, these crystals A and B cannot be put into practical use, because their crystalline forms are apt to change during their long-term preservation which passes a high temperature condition or when their pharmaceutical manufacturing steps require a high temperature treatment, thus posing a difficulty in keeping their stability as pharmaceutical preparations.

In addition to the above, the crystal A was also unstable against light.

SUMMARY

Taking these circumstances into consideration, the inventors of the present invention have conducted intensive studies with the aim of developing a pharmaceutical preparation by which the compound (I) can be put into practical use and found, as the result, that a monohydrate crystal in the form of a novel crystalline form is present with respect to the free acid compound (I) and that only this monohydrate crystal has such an unexpected stability that it can be put into practical use and it can be made into a stable solid pharmaceutical preparation. More surprisingly, it was found that this monohydrate crystal includes two crystals D and E having different dehydration temperatures (namely, two crystals D and E which have the same crystalline form according to the powder X-ray diffraction spectrum data but have different dehydration temperatures), that both of the two monohydrate crystals have excellent stability and that, of these two types of crystals, the low temperature type crystal D is suitable for the industrial production. The present invention was accomplished based on these findings.

Accordingly, the present invention provides a crystal selected from the group consisting of crystal D and crystal E of monohydrate of the compound (I), wherein these crystals are characterized by the following data of powder X-ray diffraction spectrum and TG-DSC thermogravimetric analysis.

(1) Crystal D a. It shows the lattice spacing and relative intensity shown in the following Table 1 in the powder X-ray diffraction spectrum obtained by using Cu-Kα ray.

TABLE 1

| Lattice spacing (Å) | Relative intensity |
| --- | --- |
| 8.77 ± 0.10 | medium |
| 6.50 ± 0.05 | " |
| 5.73 ± 0.03 | " |
| 5.48 ± 0.04 | strong |
| 5.21 ± 0.03 | medium |
| 4.86 ± 0.03 | " |
| 4.73 ± 0.03 | strong |
| 4.42 ± 0.03 | medium |
| 4.37 ± 0.03 | " |
| 3.38 ± 0.02 | slightly strong |
| 3.23 ± 0.02 | strong |
| 3.19 ± 0.02 | medium | b. It has a dehydration peak temperature of 135° to 149° C. according to TG-DSC thermogravimetric analysis.

(2) Crystal E a. It shows the lattice spacing and relative intensity shown in the above Table 1 in the powder X-ray diffraction spectrum obtained by using Cu-Kα ray.

b. It has a dehydration peak temperature of 160° to 170° C. according to TG-DSC thermogravimetric analysis.

The present invention also provides a solid pharmaceutical preparation which comprises the crystal D or E and a carrier for solid pharmaceutical preparation.

The following describes in detail the novel crystalline forms of the present invention, i.e., crystals D and E of compound (I) monohydrate.

Since the crystals D and E have the same powder X-ray diffraction pattern as described above, they are not included in the conventional concept of crystal polymorphism but have a relationship which can be regarded as a new type of crystal polymorphism.

Finding of these crystalline forms of hydrate crystal having such a new relationship which deviates from the conventional concept of crystal polymorphism is entirely beyond expectation and cannot be expected easily from the production of usual hydrate crystals. In addition, such new type crystalline forms are different from the conventional hydrate crystals and can be regarded as entirely novel crystalline forms.

Each of the crystals D and E shows 1 mole equivalent of dehydration to give the same anhydride crystal when dried at 150° C. for 3 hours. It was confirmed that the anhydride crystal obtained from crystal D (to be referred to as crystal F hereinafter) has a powder X-ray diffraction pattern which is clearly different from those of crystals D and E and that the dehydrated water was water of crystallization (cf. Tables 4 and 5 and FIGS. 4, 5 and 16).

In this instance, it was confirmed that the crystal F has a strong hygroscopic property and, therefore, cannot be used as a pharmaceutical bulk material.

The anhydride crystal F showed a clearly different powder X-ray diffraction pattern from that of the anhydride crystal C produced in accordance with the procedure of Example 5 of the aforementioned published patent application and, therefore, was a novel anhydride crystal which has a crystal polymorphism relationship with anhydride crystal C (cf. Tables 4 and 5 and FIGS. 3 and 16).

In consequence, each of the monohydrate crystals D and E of the present invention is a novel crystal in which 1 mole of water of crystallization is added to a novel anhydride crystal which has a relationship with known anhydride crystal in terms of crystal polymorphism and, therefore, is a crystalline form of new concept that cannot be found in the prior art hydrate crystals.

The novel crystals D and E of monohydrate of compound (I) of the present invention are specified by the aforementioned physicochemical properties which, however, should not be taken strictly because of the nature of their powder X-ray diffraction spectrum data. For the identity confirmation of crystals, crystal lattice spacing and general pattern are important and the relative intensity will change to some extent depending on the direction of crystal growth, particle size and measuring conditions.

(Production method)

The monohydrate crystals D and E of the present invention can be produced by recrystallization which is one of the commonly used methods for the production of hydrate crystals. With regard to the crystal to be used in crystallization, various crude crystals of free acid of compound (I) may preferably be used, but the anhydride crystal produced in accordance with the procedure of Example 5 of the aforementioned published patent application, an anhydride crystal obtained by dehydrating each of crystals D and E, or a crystal of other free acid compound (I) can also be used.

Crystallization is carried out by dissolving the crystal in a solvent suitable for the crystallization of the monohydrate, preferably in aqueous hydrochloric acid solution, effecting the crystallization under a mild condition, preferably by gradually cooling the heat-dissolved solution under a mildly stirring condition, and drying the crystals preferably at 40° to 60° C. under a reduced pressure.

In order to obtain either one of the monohydrate crystals D and E of the present invention with a high reproducibility, it is advantageous to obtain it under the following respectively specified conditions.

(1) Crystal D

Crystal D is apt to crystallize in a large scale (kg order) synthesis.

Solvent: 1N hydrochloric acid, 37 to 40 times amount

Agitation: slow agitation with a mechanical stirrer (about 110 rpm)

Cooling: gradual cooling

Drying: drying at 40° to 60° C. under reduced pressure

In this instance, since the above conditions can be changed slightly depending on the synthesizing scale and difference in equipments, it is desirable to adjust these conditions appropriately.

Alternatively, as is clear from the following Example 3, crystal D can also be produced from anhydride crystal of the compound (I) by 3 hours or more of suspension stirring of the anhydride crystal in water to effect conversion.

(2) Crystal E

Crystal E is apt to crystallize in a laboratory scale (g order).

Solvent: 1N hydrochloric acid, 37 to 40 times amount

Agitation: agitation with a magnetic stirrer at such a slow rate that the liquid surface does not create a whirlpool Cooling: gradual cooling (without using an ice bath and the like)

Drying: drying at 40° to 60° C. under reduced pressure

In this instance, since the above conditions may sometimes result in the formation of crystal D or a mixture of crystals D and E depending on slight changes in the synthesizing scale, equipment and agitation and cooling conditions, it is desirable to adjust each of the conditions appropriately.

In consequence, when put into practical use as a solid pharmaceutical preparation, crystal D which is suitable for the large scale synthesis is more advantageous.

The present invention also includes a solid pharmaceutical preparation which contains the thus produced crystal D or E of monohydrate of compound (I) as an active ingredient.

Examples of the dosage form of the solid pharmaceutical preparation of the present invention include powders, fine subtilaes, granules, tablets, pills, capsules, suppositories and the like, and these solid preparations may be prepared by the usual way using pharmaceutically acceptable carriers, vehicles, binders, lubricants, disintegrators, coating agents, coloring agents, flavoring agents and other additive .agents which are commonly used in the production of solid pharmaceutical preparations.

Illustrative examples of the above carriers and other additive agents include starch, lactose, crystalline cellulose, mannitol, sorbitol, sucrose, calcium sulfate, calcium lactate, synthetic aluminum silicate, dibasic calcium phosphate, anhydrous silicic acid, magnesium aluminate metasilicate, carboxymethylcellulose calcium, magnesium stearate, talc, plant oil, fatty acid (mono, di or tri) glyceride, hydrogenated plant oil, hydroxypropylcellulose and the like.

The solid pharmaceutical preparation of the present nvention may be administered orally in the aforementioned dosage form such as tablets and the like or parenterally as the aforementioned suppositories, for the treatment of the diseases described in the aforementioned JP-A-2-138288, within a range of dose which is also disclosed in the same published patent application. However, its dose is not particularly limited to the disclosed range, because smaller dose may be effective in some cases depending on the symptoms and the like.

BEST MODE OF CARRYING OUT THE INVENTION

Figure 1:
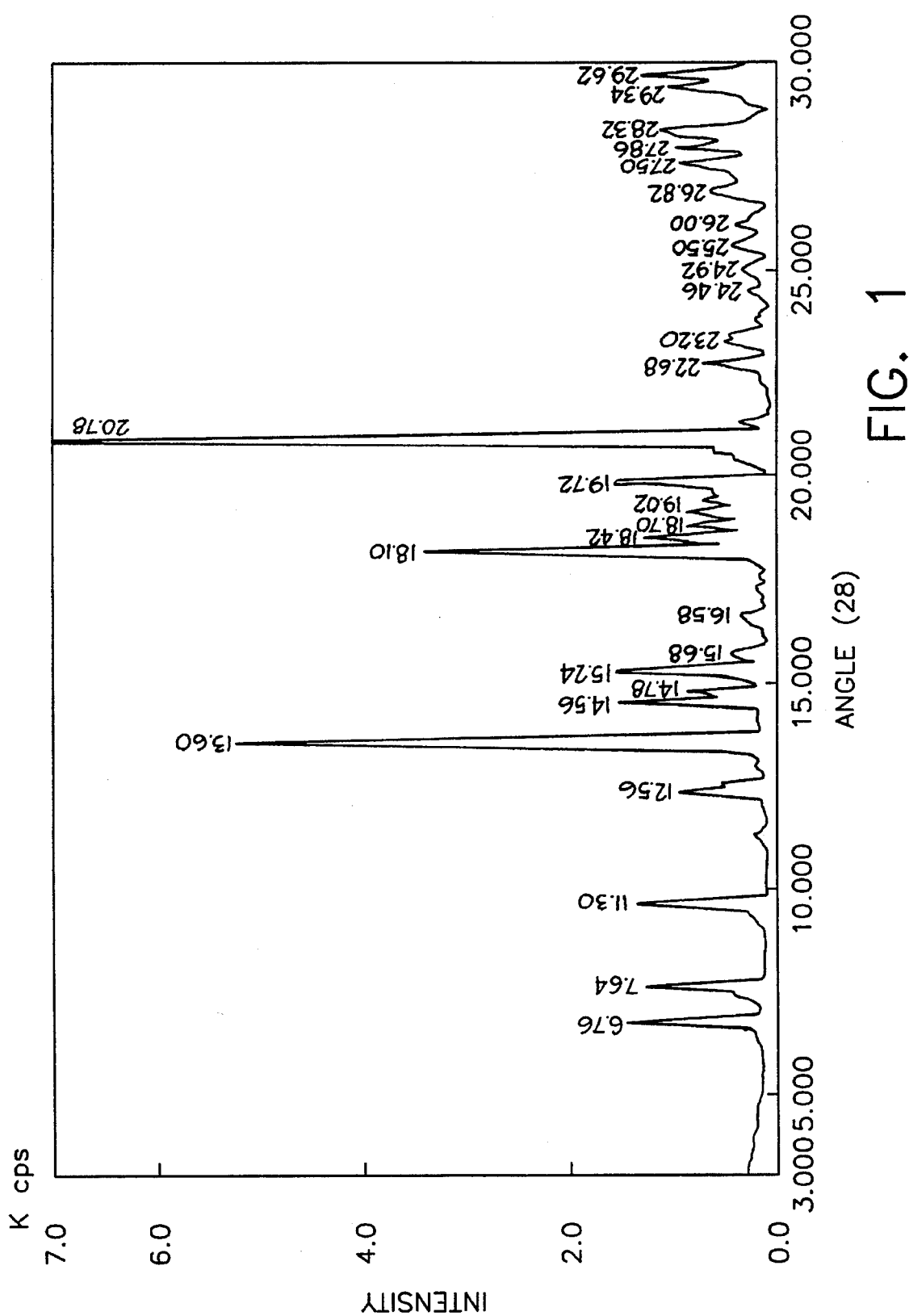
FIGS. 1 to 5 respectively show powder X-ray diffraction spectra of crystals A to E, FIGS. 6 to 10 respectively show charts of the TG-DSC thermogravimetric analysis of crystals A to E, FIGS. 11 to 15 respectively show infrared absorption spectra of crystals A to E.

The following describes production examples of the aforementioned comparative crystals A to C and monohydrate crystals D and E of the present invention.

REFERENCE EXAMPLE 1

Production Example of Crystal A (Lot. T-8)

A 25.0 g portion of 1-hydroxy-2-(imidazo[ 1,2-a]pyridin-3-yl)ethane-1,1-bis(phosphonic acid) monosodium salt 2.2 hydrate was added to 300 ml of distilled water and dissolved with heating, and, after cooling to 40° C., the resulting solution was adjusted to pH 5.39 with aqueous 1N sodium hydroxide solution. The solution was again heated, and, when its temperature reached 86° C., 180 ml of ethanol was added dropwise for 5 minutes, subsequently allowing the resulting solution to stand overnight at room temperature. Crystals thus precipitated were collected by filtration, washed twice with 180 ml of ethanol and then dried at 50° C. for 7 hours under a reduced pressure to obtain 20.6 g of crystals. A 19.87 g portion of the thus obtained product was allowed to stand for 1 day over the beaker filled with saturated aqueous sodium chloride solution in a desiccator, thereby obtaining 20.43 g of monosodium 1-hydroxy-2-(imidazo[1,2-a]pyridin-3-yl)ethane-1,1-bis(phosphonate) dihydrate in the form of white columnar crystals.

REFERENCE EXAMPLE 2

Production Example of Crystal B (Lot. T-10)

An 8.0 g portion of 1-hydroxy-2(imidazo-[ 1,2-a]pyridin-3-yl)ethane-1,1-bis(phosphonic acid) monohydrate was suspended in 70 ml of distilled water and, after adding 24 ml of 1N sodium hydroxide aqueous solution at room temperature, dissolved with heating, subsequently filtering the solution through a cotton plug. The filtrate was cooled to 40° C., adjusted to pH 5.36 with 1N sodium hydroxide aqueous solution and then heated again. A 55 ml portion of ethanol was added to the solution when its temperature reached 86° C., the resulting mixture was allowed to stand for 2 days at room temperature and then the crystals thus precipitated were collected by filtration. After washing twice with 50 ml of ethanol, they were dried at 55° C. for 7 hours under a reduced pressure to obtain 7.55 g of crystals. The thus obtained product was allowed to stand for 2 days over the beaker filled with saturated sodium chloride solution in a desiccator, thereby obtaining 7.98 g of monosodium 1-hydroxy-2-(imidazo[1,2-a]pyridin-3-yl)ethane- 1,1-bis(phosphonate) trihydrate as white needle crystals.

REFERENCE EXAMPLE 3

Production Example of Crystal C (Lot. 49-1)

A 5 g portion of partially purified 1-hydroxy-2-(imidazo-[ 1,2-a]pyridin-3-yl)ethane-1,1-bis(phosphonic acid) was dissolved in 20 ml of 6N hydrochloric acid with heating. After adding 80 ml of methanol with heating, the resulting mixture was rapidly cooled with an ice water bath. Three hours thereafter, the thus formed precipitate was collected by filtration, washed with 50 ml of methanol, and dried at 50° to 60° C. under a reduced pressure to obtain 3.8 g of 1-hydroxy-2-(imidazo[1,2-a]pyridin-3-yl )ethane-1,1-bis-(phosphonic acid) white crystal having ½ mole free water.

Example 1

Production Example of Crystal D (Lot. H-1)

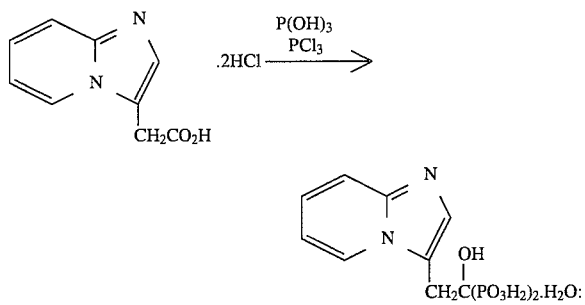

A 32.5 kg portion of imidazo[1,2-a]pyridin-3-y-lacetic acid dihydrochloride and 31.8 kg of phosphorous acid were added to 480 kg of chlorobenzene, and the resulting mixture was stirred for 30 minutes at 110° C. A 82.9 kg portion of phosphorous trichloride was added to the reaction mixture at 80° to 100° C. and then the whole mixture was stirred for 8 hours at 110° to 120° C. The separated chlorobenzene layer was removed from the reaction mixture, and 530 l of 6N hydrochloric acid was added to the resulting residue and the solution was heated under reflux for 2 hours. The reaction mixture was mixed with activated carbon and filtered. The filtrate was concentrated under a reduced pressure. The residue was mixed with 300 l of water and the solution was concentrated under a reduced pressure. The resulting residue was mixed with 180 l of 1N hydrochloric acid and stirred overnight at 0° C. The thus formed crystals were collected by filtration, washed with 40 l of water and 30 l of methanol in that order and then dried to obtain 25.9 kg of crude crystals. A 22.5 kg portion of the crude crystals were added to 900 l of 1N hydrochloric acid and dissolved with heating, followed by filtration. With stirring at 110 rpm, the resulting filtrate was cooled down from 101° C. to 36.8° C. for 3 hours and 20 minutes and then to 20.9° C. for overnight. The yielded crystal was collected by filtration, washed with 50 l of water and 50 l of ethanol in that order and then dried at 45° C. under a reduced pressure to obtain 19.6 kg of 1-hydroxy-2-(imidazo[1,2-a]pyridin-3-yl)ethane-1,1-bis-(phosphonic acid) monohydrate. The final yield was 50.9%.

Example 2

Production Example of Crystal E (Lot. T-4)

A 20.0 g portion of 1-hydroxy-2(imidazo-[ 1,2-a]pyridin-3-yl)ethane-1,1-bis(phosphonic acid) monohydrate was dissolved in 750 ml of 1N hydrochloric acid with heating under reflux, and the resulting solution was filtered through a cotton plug and then stirred overnight at room temperature. The crystals thus precipitated were collected by filtration, washed with methanol and then dried at 50° C. for 67 hours under a reduced pressure to obtain 16.35 g of 1-hydroxy-2-(imidazo[1,2-a]pyridin-3-yl)ethane- 1,1-bis(phosphonic acid) monohydrate in the form of white powder crystals.

Powder X-ray diffraction spectra of the crystals A to E obtained above are respectively shown in FIGS. 1 to 5, their TG-DSC thermogravimetric analysis charts are respectively shown in FIGS. 6 to 10 and their infrared absorption spectra are respectively shown in FIGS. 11 to 15.

Conditions for these measurements are as follows.

(1) Powder X-ray diffraction spectrum
Apparatus: RINT-1400 powder X-ray diffraction analyzer manufactured by Rigaku Denki, target: Cu, filter: Ni, voltage: 40 kV, current: 40 mA, scan speed: 3.0°/min.

(2) TG-DSC thermogravimetric analysis
Apparatus: TG-DSC.(TAS-100) thermal analyzer manufactured by Rigaku Denki, sample amount: about 10 mg, sample cell: aluminium open cell, nitrogen gas flow: 50 ml/min., temperature increase rate: 10°/min.

(3) Infrared absorption spectrum
Apparatus: Hitachi 260-50 infrared spectrophotometer, KBr method Also, physicochemical properties of the crystals A to E and data on their crystalline forms are respectively summarized in Tables 3 and 4.

Figure 17:
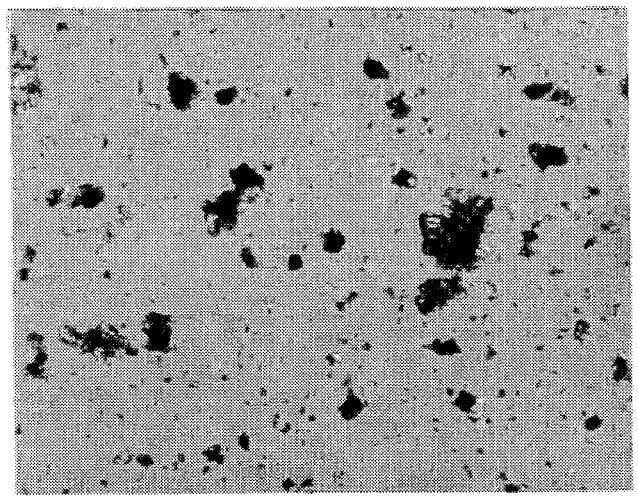
Figure 18:
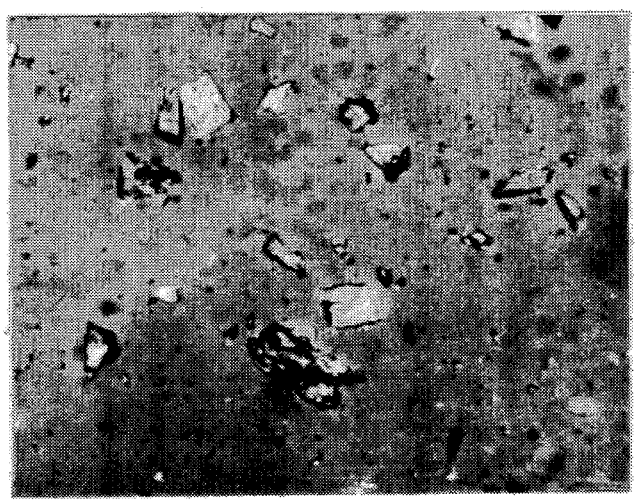
Figure 19:
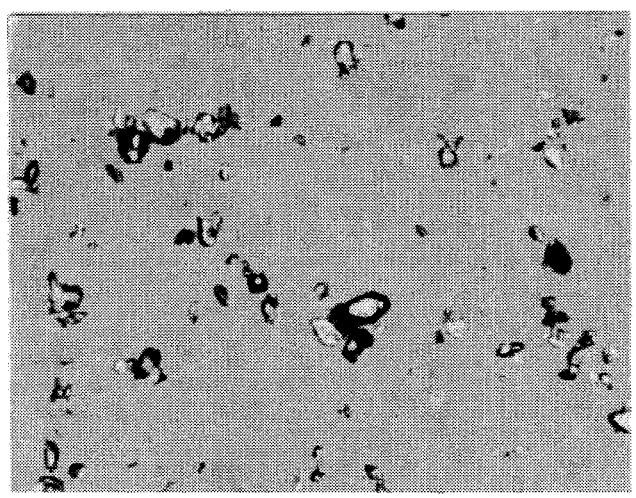

In this instance, it is evident from the polarization microphotographs shown in FIGS. 17 to 19 that the known crystal C is microscopically a small plate lump, while the crystals D and E are plate or columnar crystals.

TABLE 3

| | Physicochemical properties | | | | | |
|---|---|---|---|---|---|---|
| Crystal code | A (Lot. T-8) | | B (Lot. T-10) | | C (Lot. 49-1) | |
| Crystal water | 2 moles | | 3 moles | | anhydrous (½ mole) | |
| Molecular formula | $C_9H_{11}N_2O_7P_2Na.2H_2O$ | | $C_9H_{11}N_2O_7P_2Na.3H_2O$ | | $C_9H_{12}N_2O_7P_2.½H_2O$ | |
| Elemental analysis | calcd. | found | calcd. | found | calcd. | found |
| C | 28.43% | 28.32% | 27.15% | 27.08% | 32.64% | 32.73% |
| H | 3.98 | 3.78 | 4.30 | 4.19 | 3.96 | 3.83 |
| N | 7.37 | 7.31 | 7.04 | 7.07 | 8.46 | 8.47 |
| P | 16.30 | 16.19 | 15.56 | 15.56 | 18.71 | 18.95 |
| Appearance* | yellowish white | | yellowish white | | white | |
| Form (polarization microscope) | plate to columnar | | needle to plate | | small plate lump | |
| Melting point | 244° C. (decomp.) | | 240° C. (decomp.) | | 250° C. (decomp.) | |
| Water content (KF method) | | | | | | |
| (theoretical) | 9.48% | | 13.57% | | 2.72% | |
| (measured) | 9.40 | | 13.45 | | 2.13 | |
| Loss on drying | | | | | | |
| 80° C., 5 hours | 2.89% | | 4.53% | | | |
| 105° C., 5 hours | 4.67 | | 9.20 | | | |

TABLE 3-continued

| | Physicochemical properties | | |
|---|---|---|---|
| 150° C., 3 hours | 7.19 | 13.51 | 2.36 |
| Hygroscopicity | | | |
| 93% RH, 1 day | 0.12% | 0.10% | 1.10% |
| 7 days | 0.19 | 0.08 | 0.92 |
| 75% RH, 1 day | 0.09 | 0.05 | 0.62 |
| 7 days | 0.06 | 0.05 | 0.47 |

| | | D (Lot. H-1) | E (Lot. T-4) |
|---|---|---|---|
| Crystal code | | 1 mole | 1 mole |
| Crystal water | | (low temp. type) | (high temp. type) |
| Molecular formula | | $C_9H_{12}N_2O_7P_2 \cdot H_2O$ | $C_9H_{12}N_2O_7P_2 \cdot H_2O$ |
| Elemental analysis | | calcd.    found | calcd.    found |
| C | | 31.78%    31.51% | 31.78%    31.66% |
| H | | 4.15    4.24 | 4.15    4.01 |
| N | | 8.24    8.08 | 8.24    8.19 |
| P | | 18.21    18.18 | 18.21    18.28 |
| Appearance* | | reddish white | reddish white |
| Form (polarization microscope) | | plate to needle | plate to needle |
| Melting point | | 250° C. (decomp.) | 250° C. (decomp.) |
| Water content (KF method) | | | |
| (theoretical) | | 5.30% | 5.30% |
| (measured) | | 5.36 | 5.32 |
| Loss on drying | | | |
| 80° C., 5 hours | | 0.00% | 0.00% |
| 105° C., 5 hours | | 3.19 | 0.61 |
| 150° C., 3 hours | | 5.50 | 5.46 |
| Hygroscopicity | | | |
| 93% RH, 1 day | | 0.04% | 0.02% |
| 7 days | | 0.10 | 0.02 |
| 75% RH, 1 day | | 0.07 | 0.02 |
| 7 days | | 0.13 | 0.02 |

*Judged in accordance with The Japanese Pharmacopoeia

TABLE 4

Figure 2:
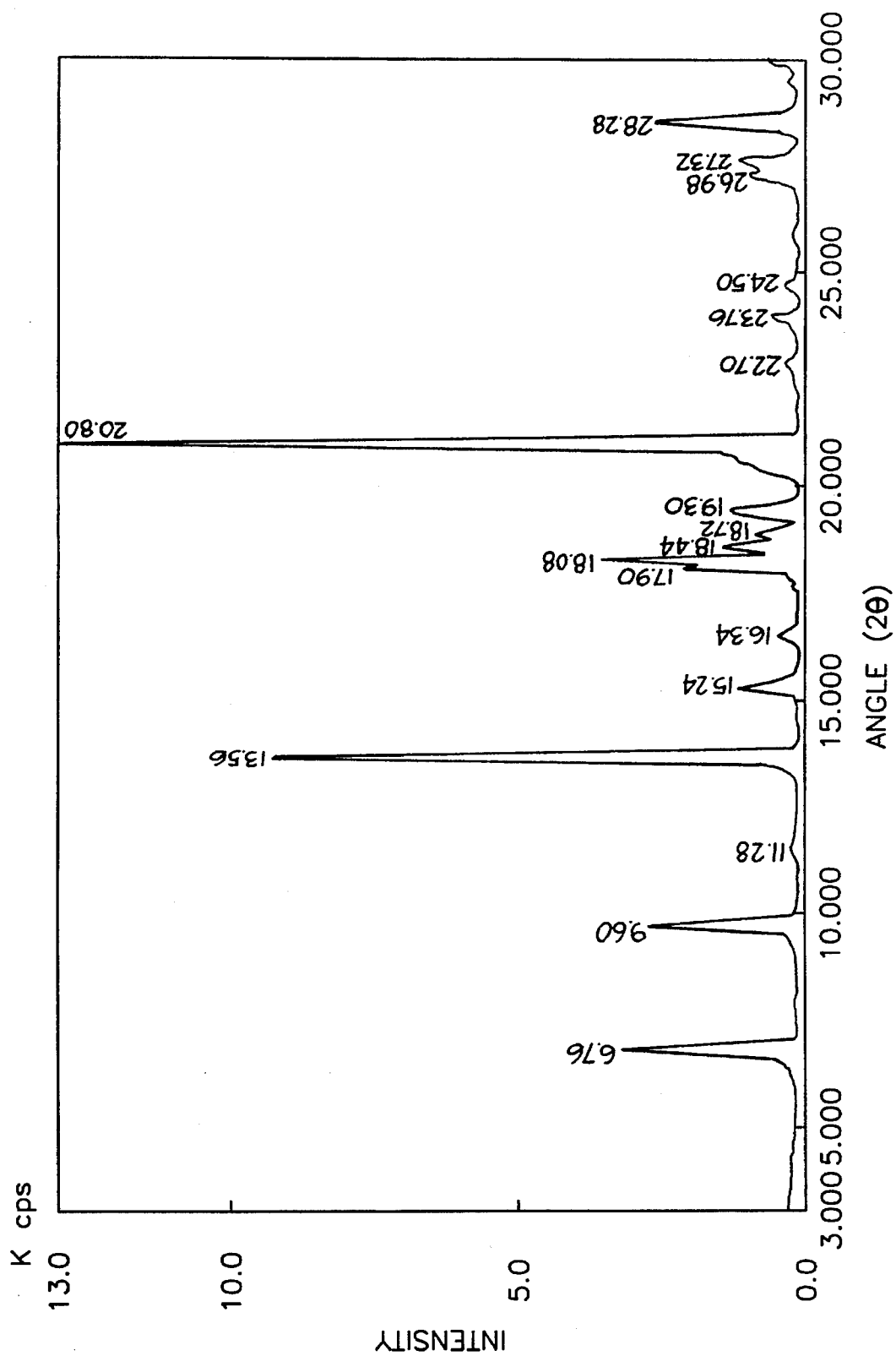
Figure 3:
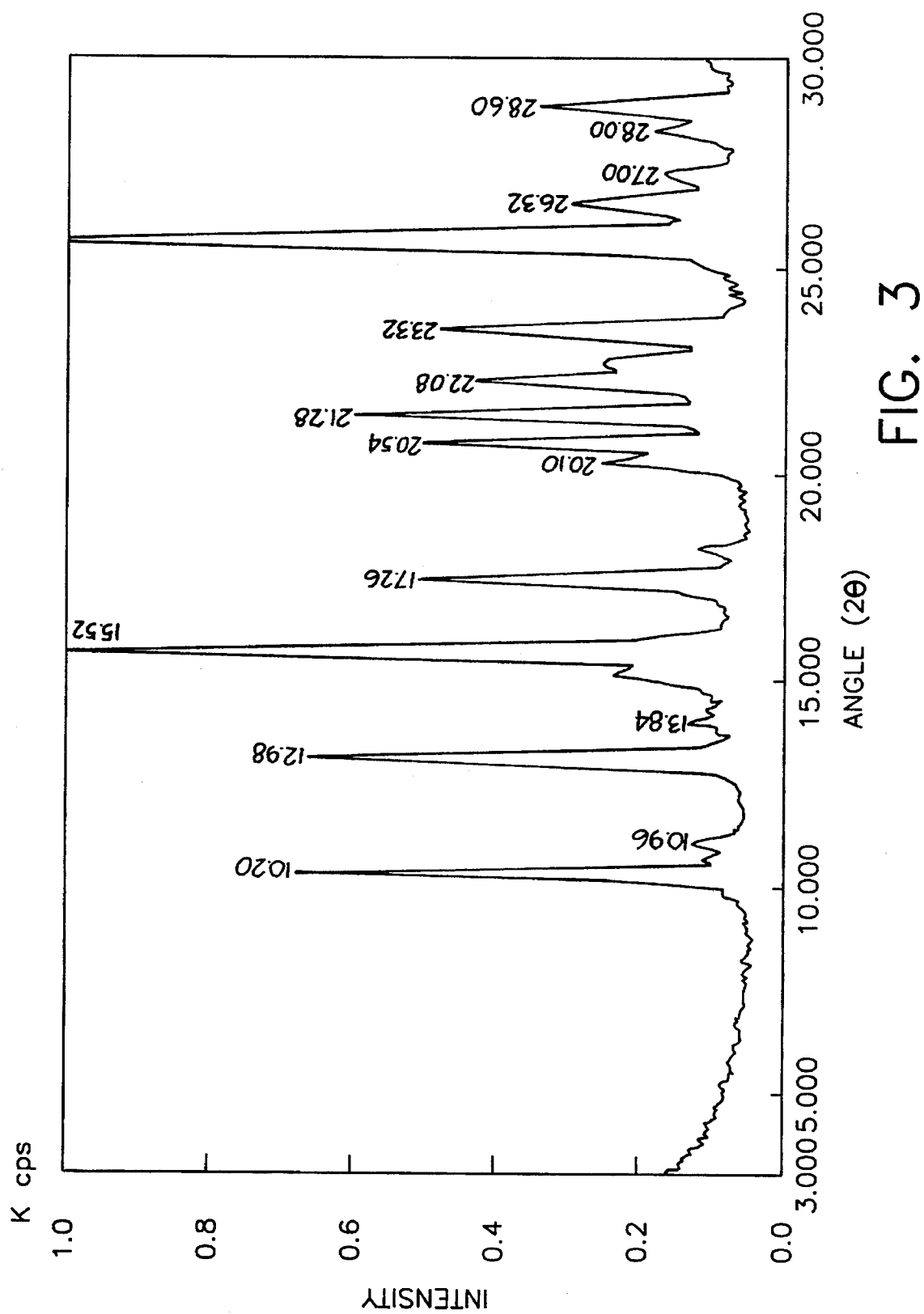
Figure 4:
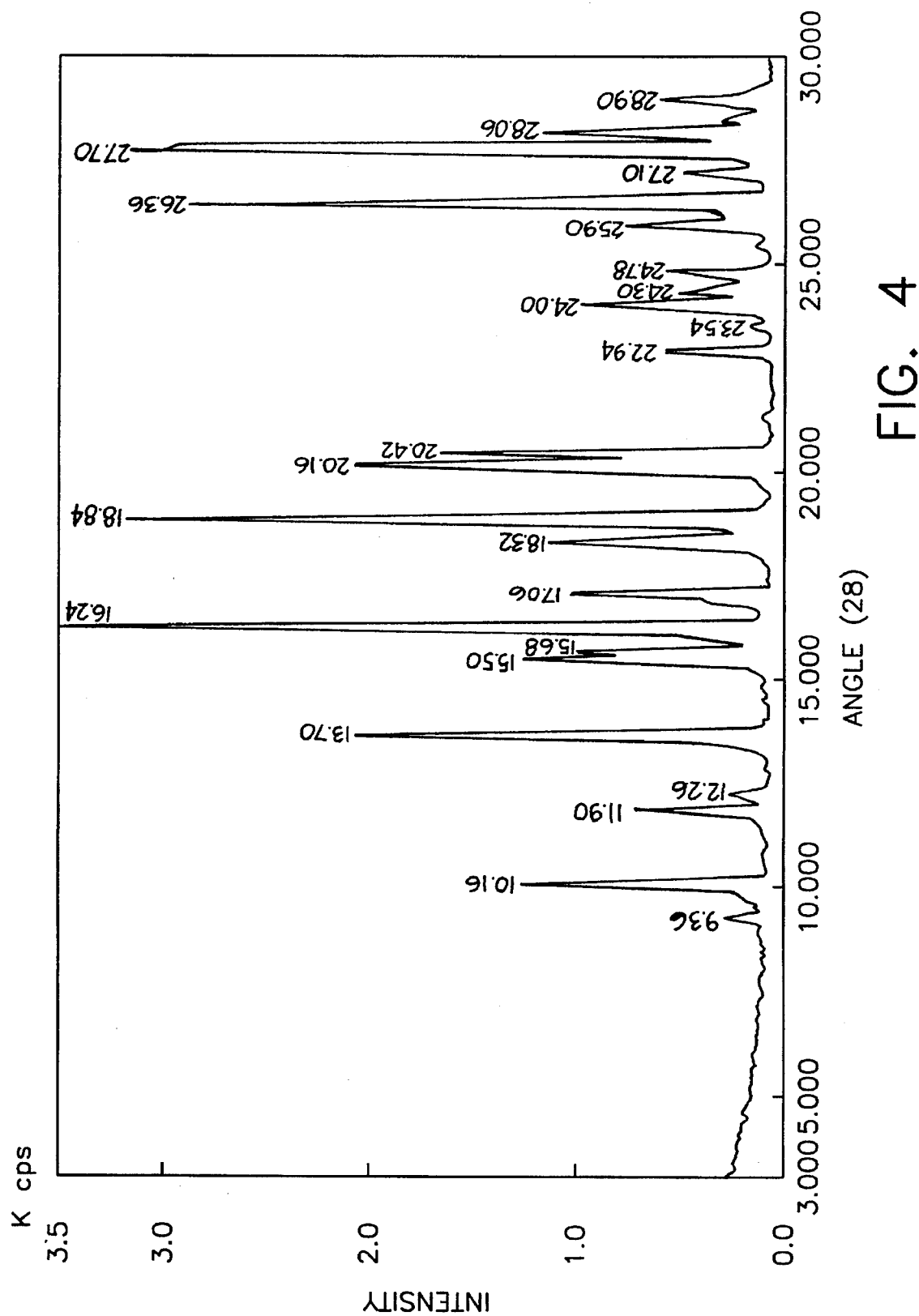
Figure 5:
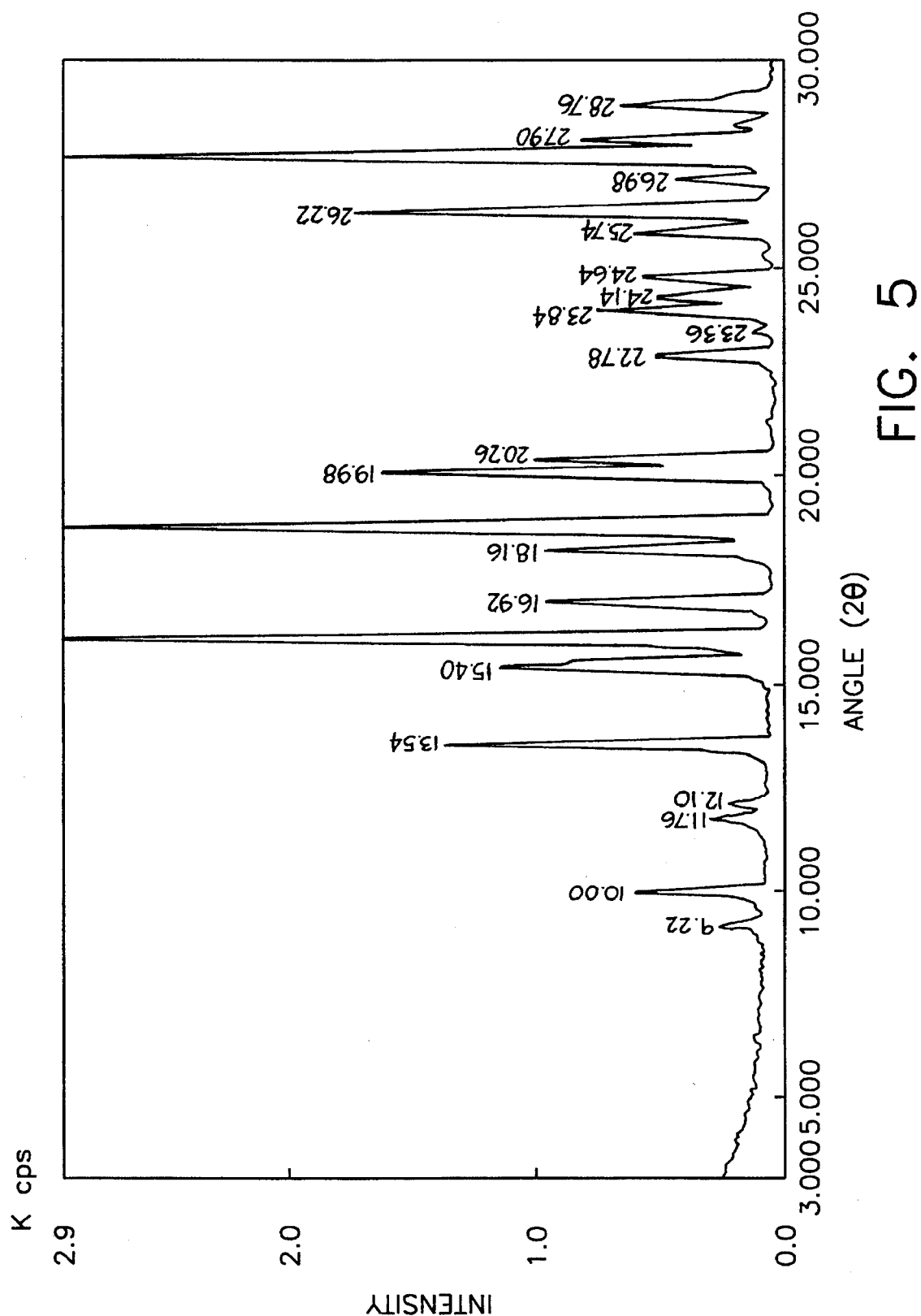
Figure 6:
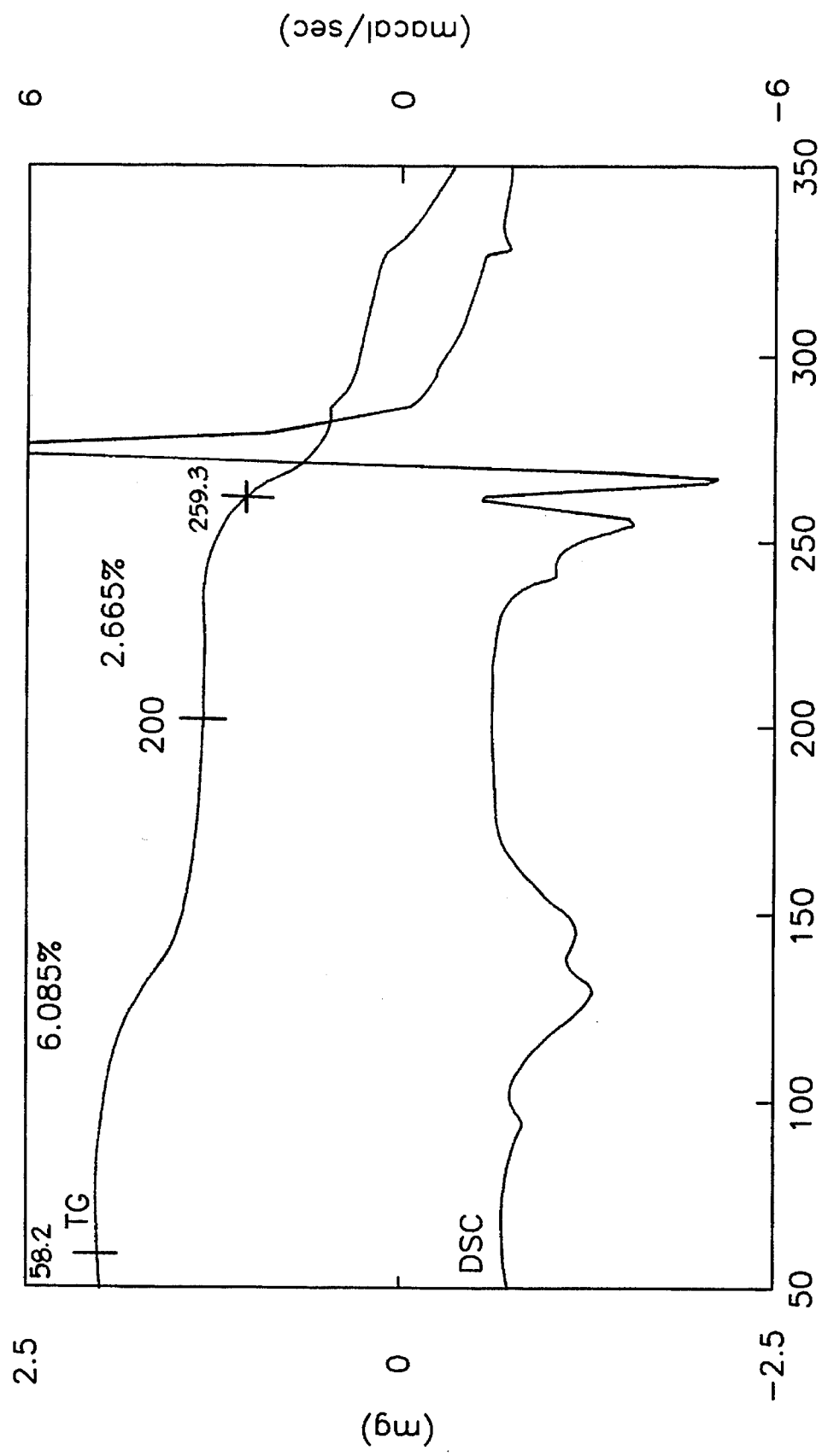
Figure 7:
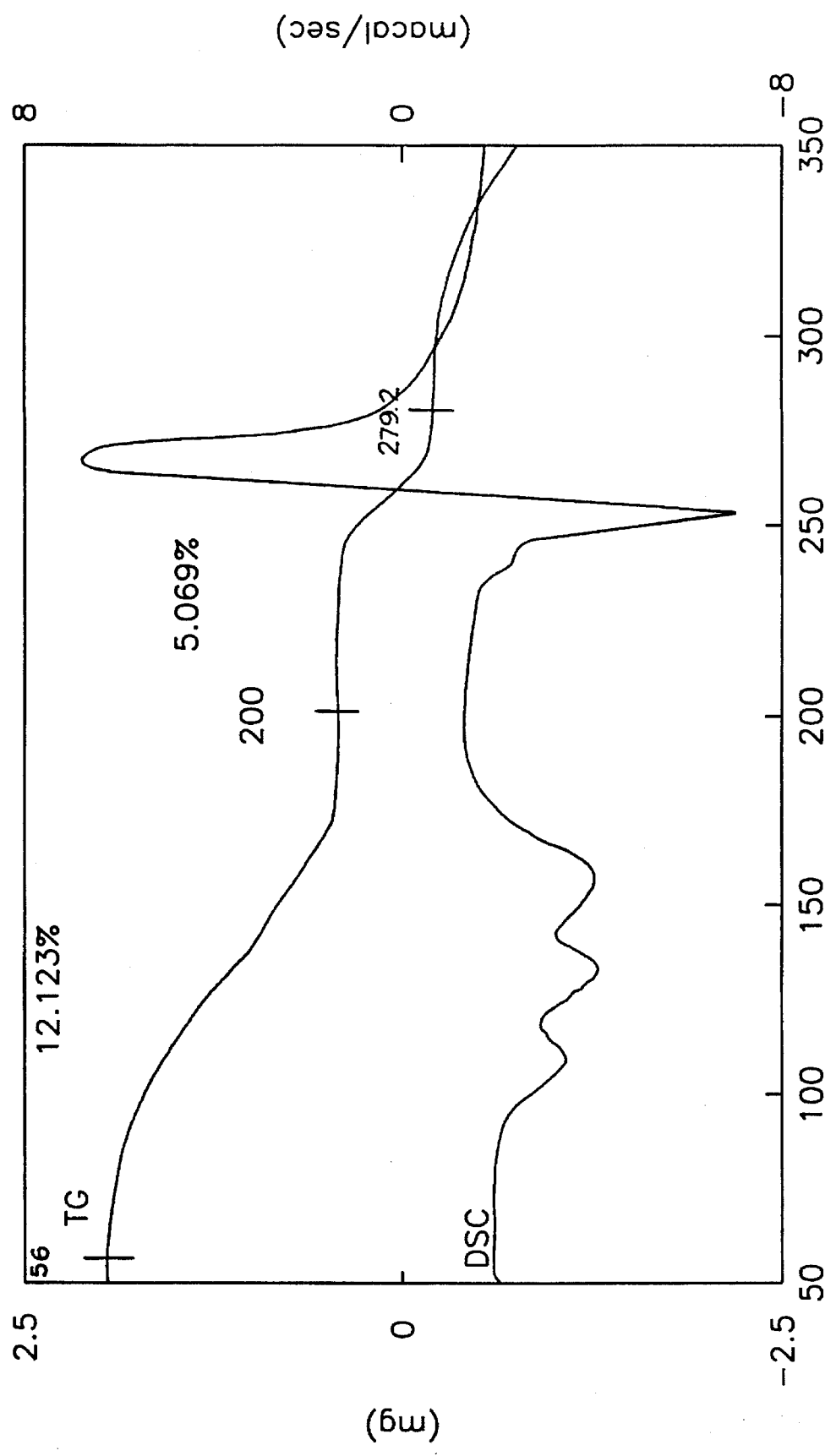
Figure 8:
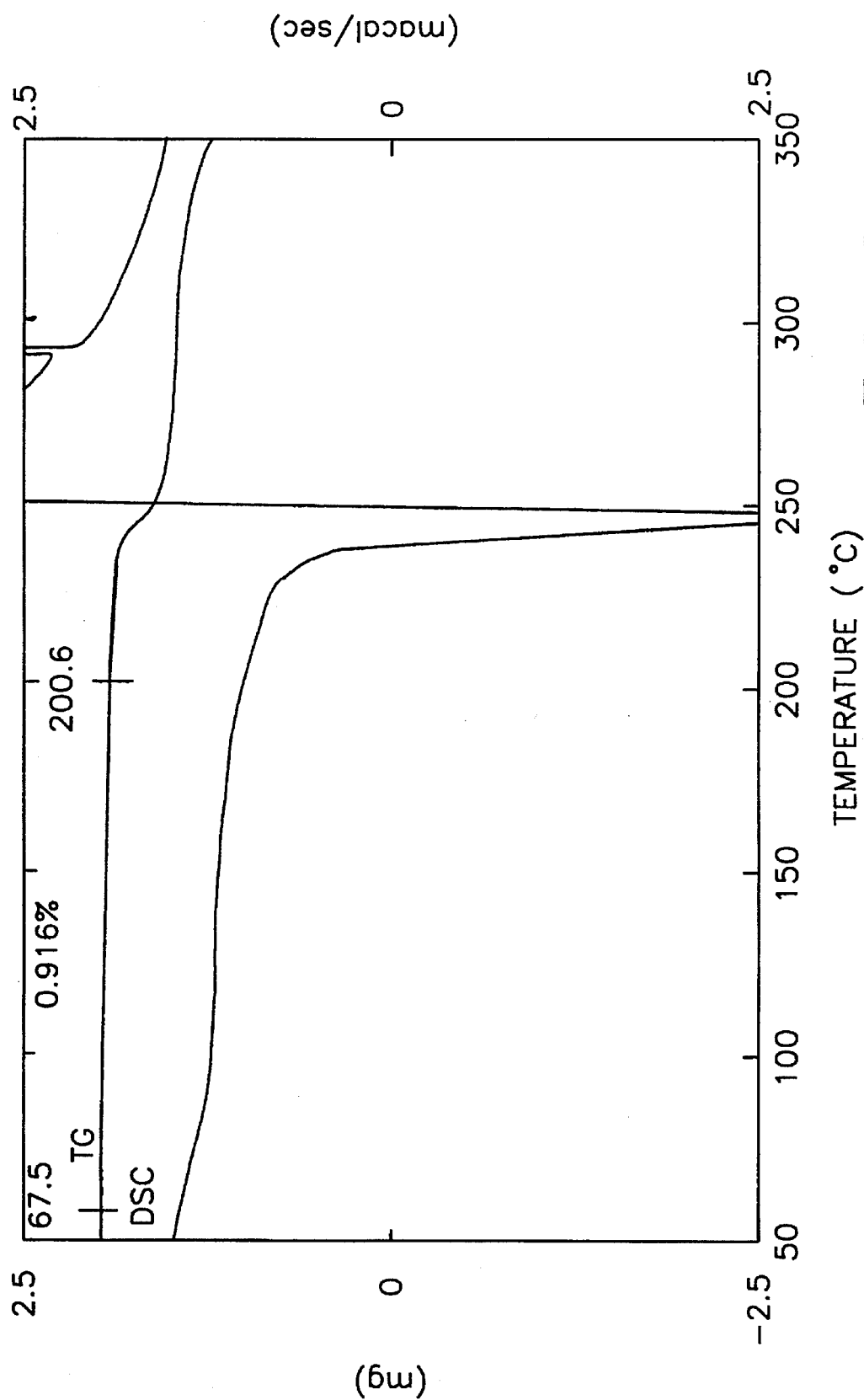
Figure 9:
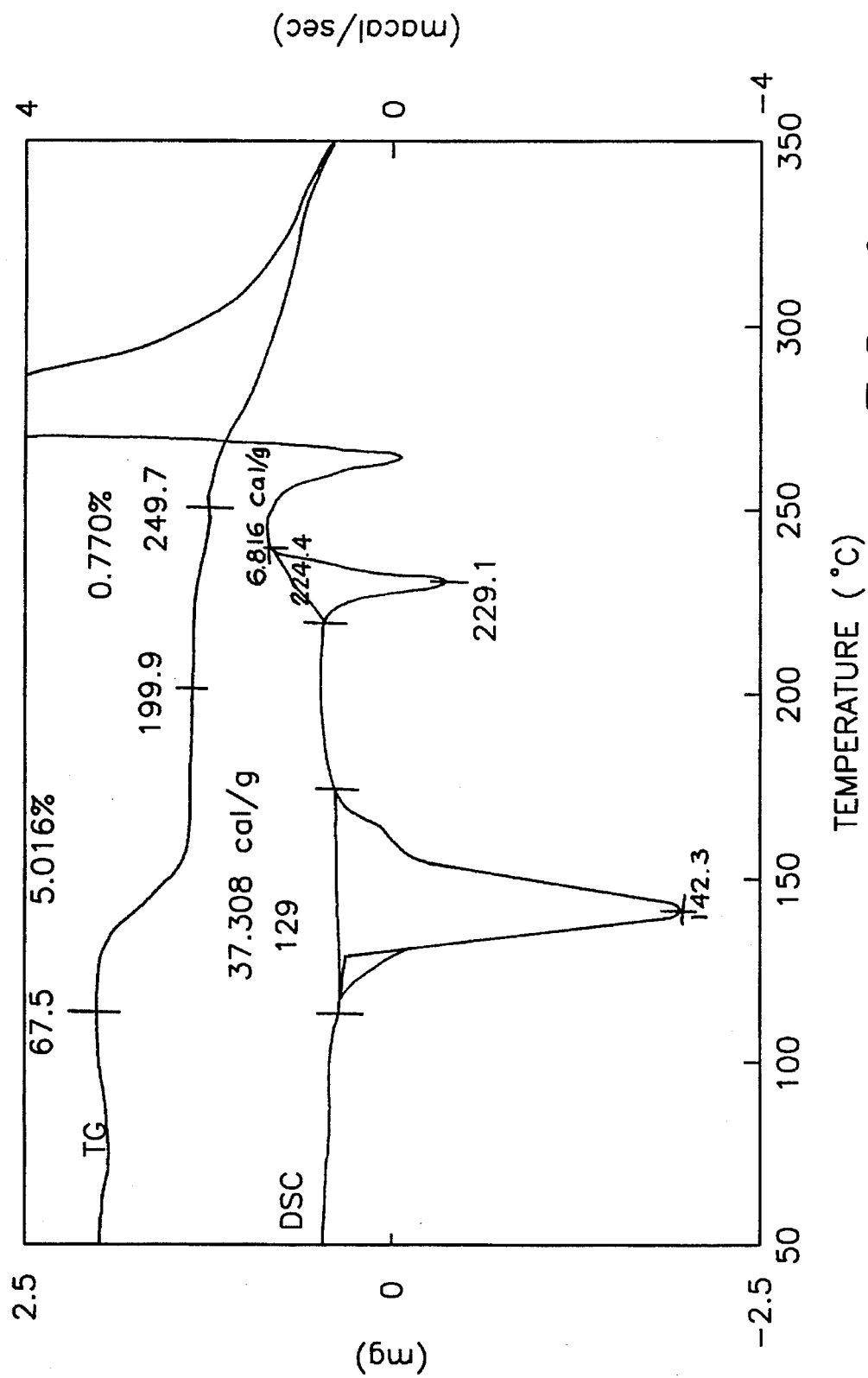
Figure 10:
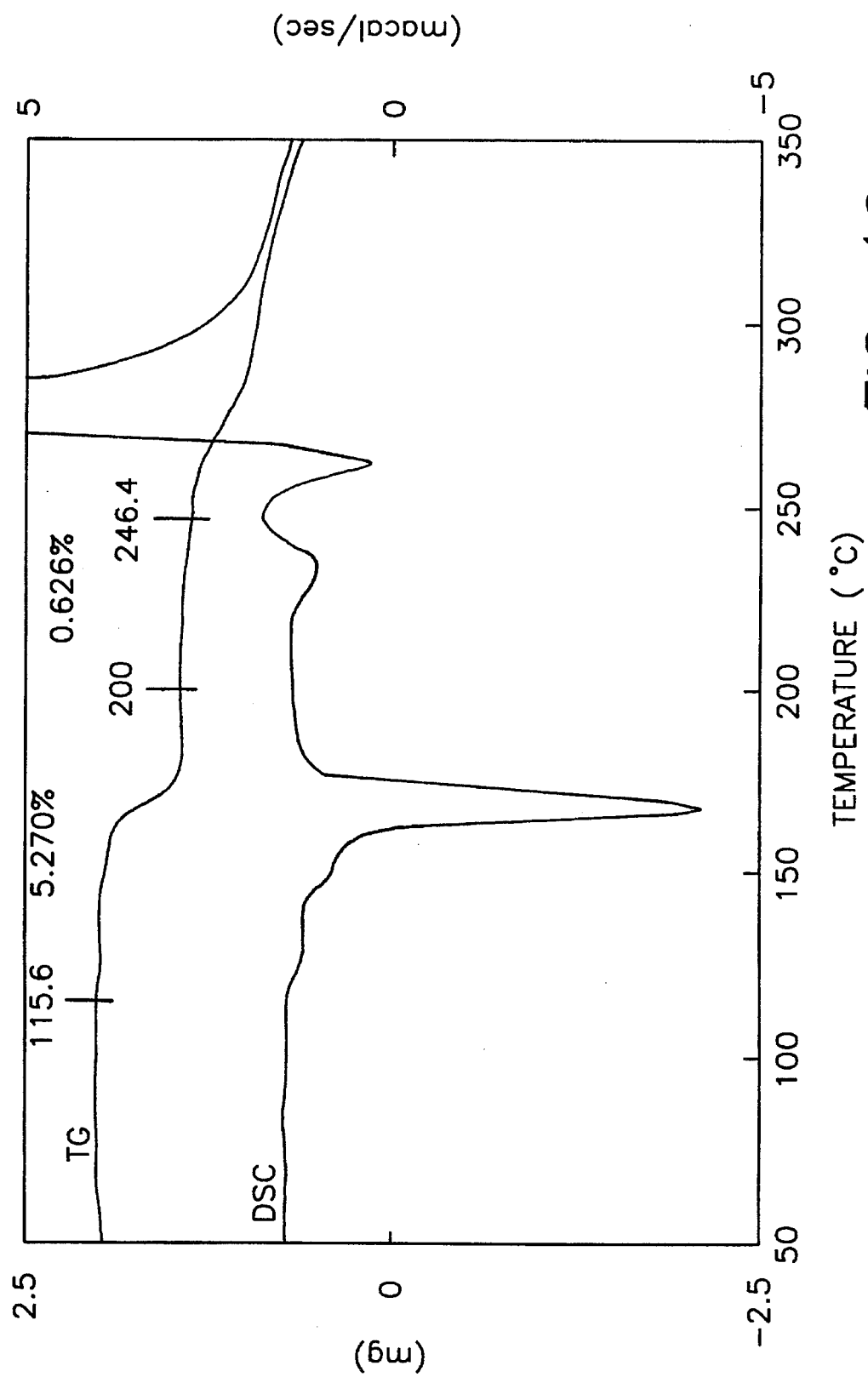
Figure 11:
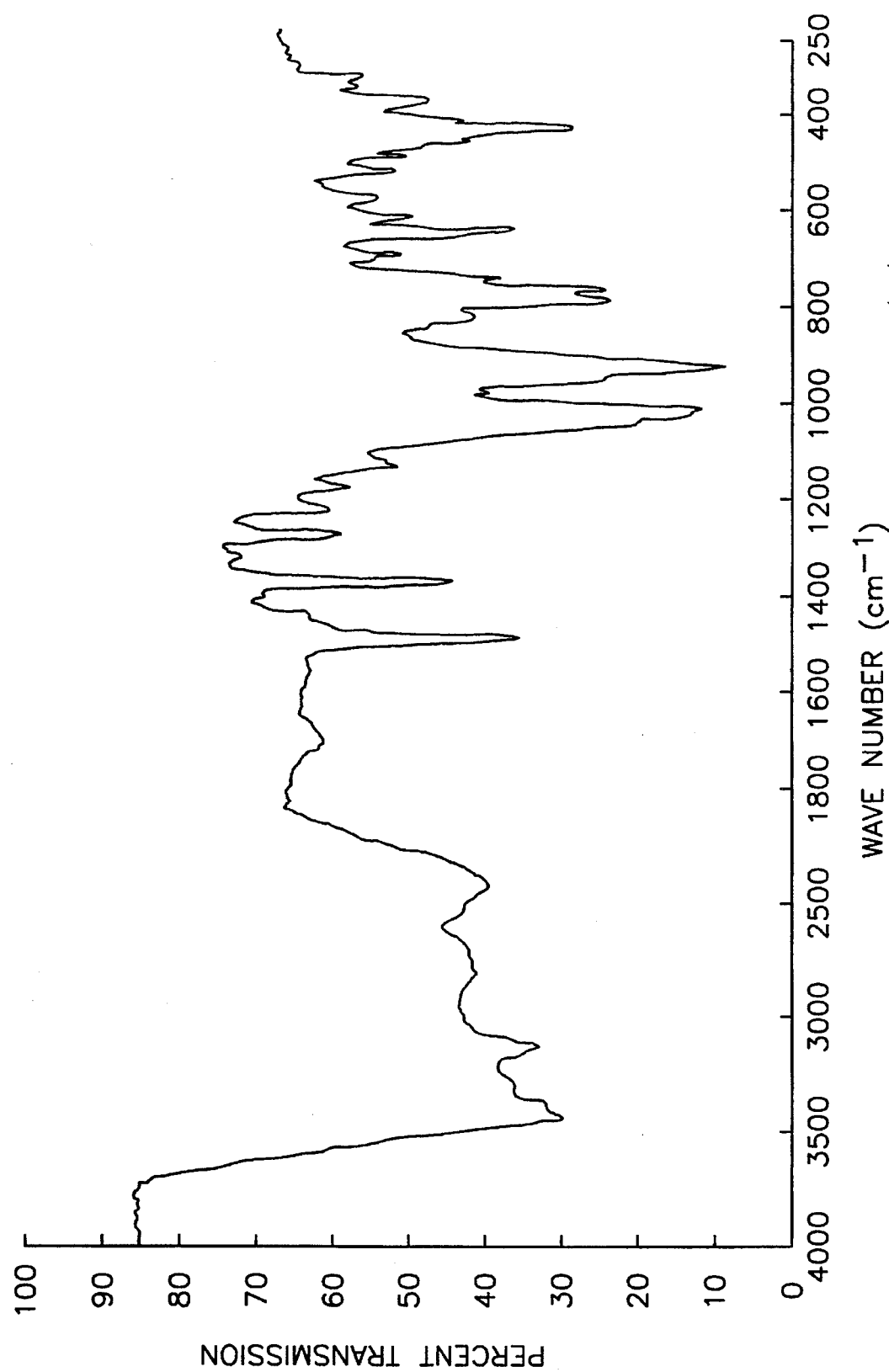
Figure 12:
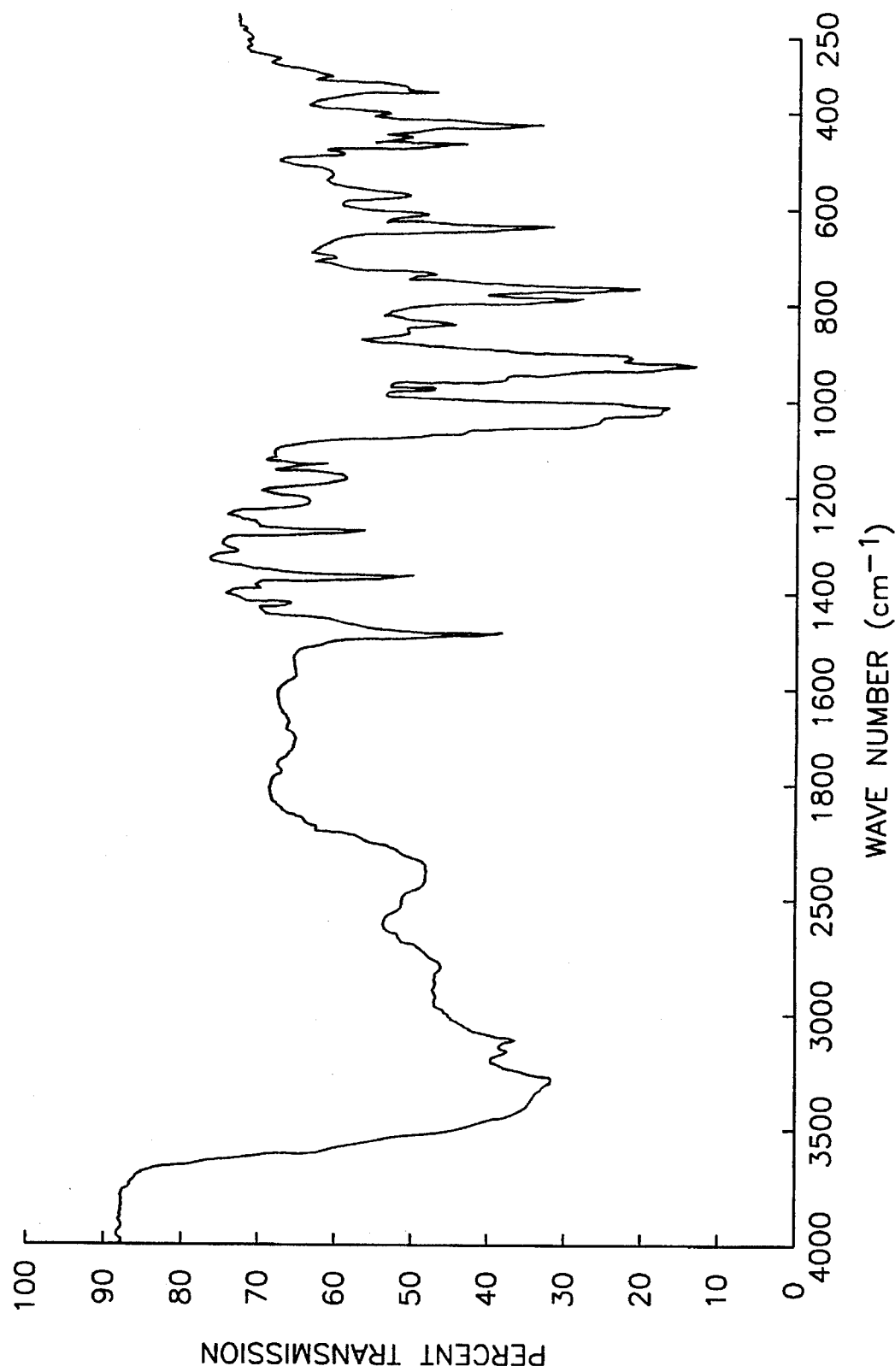
Figure 13:
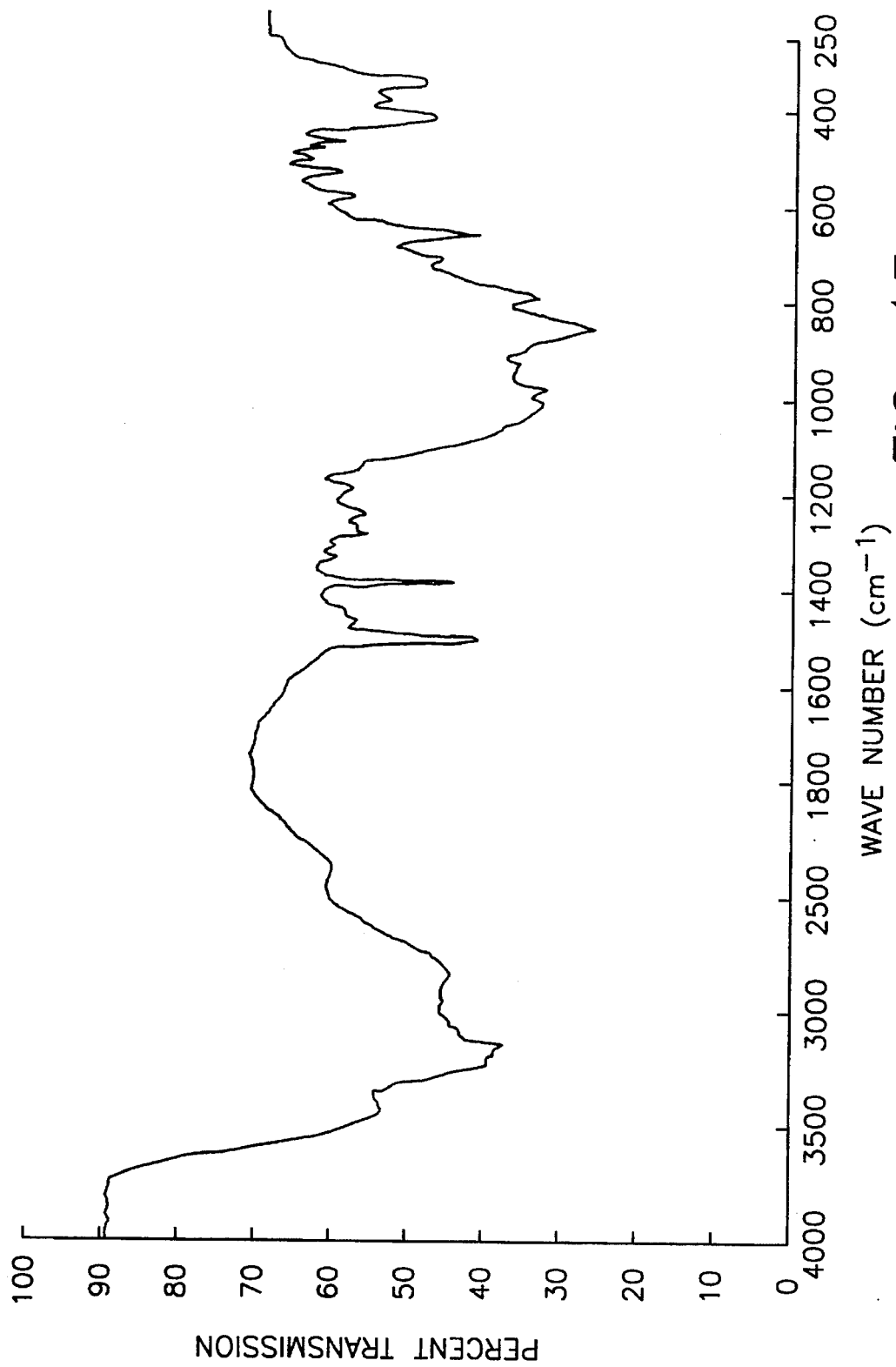
Figure 14:
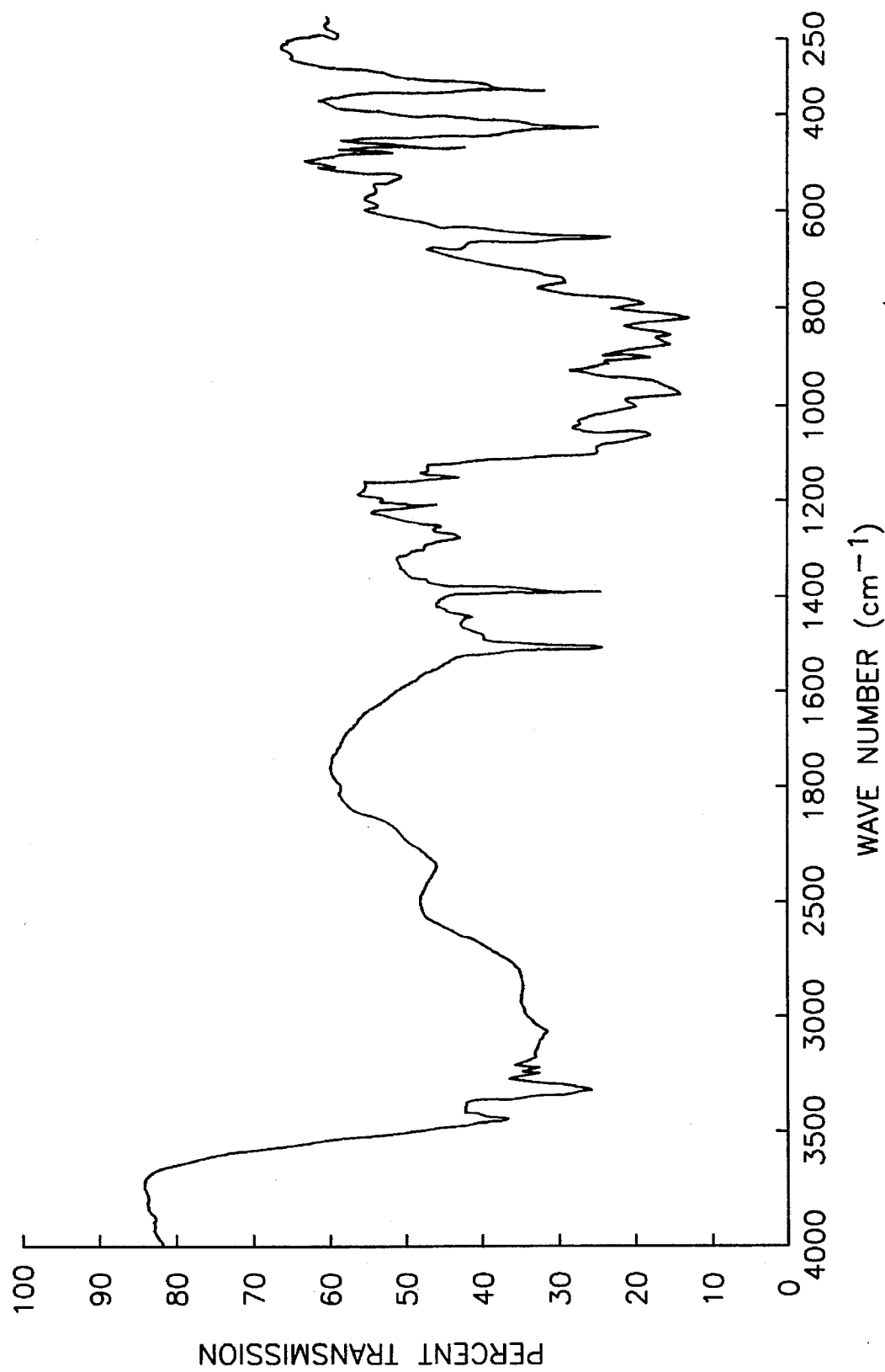
Figure 15:
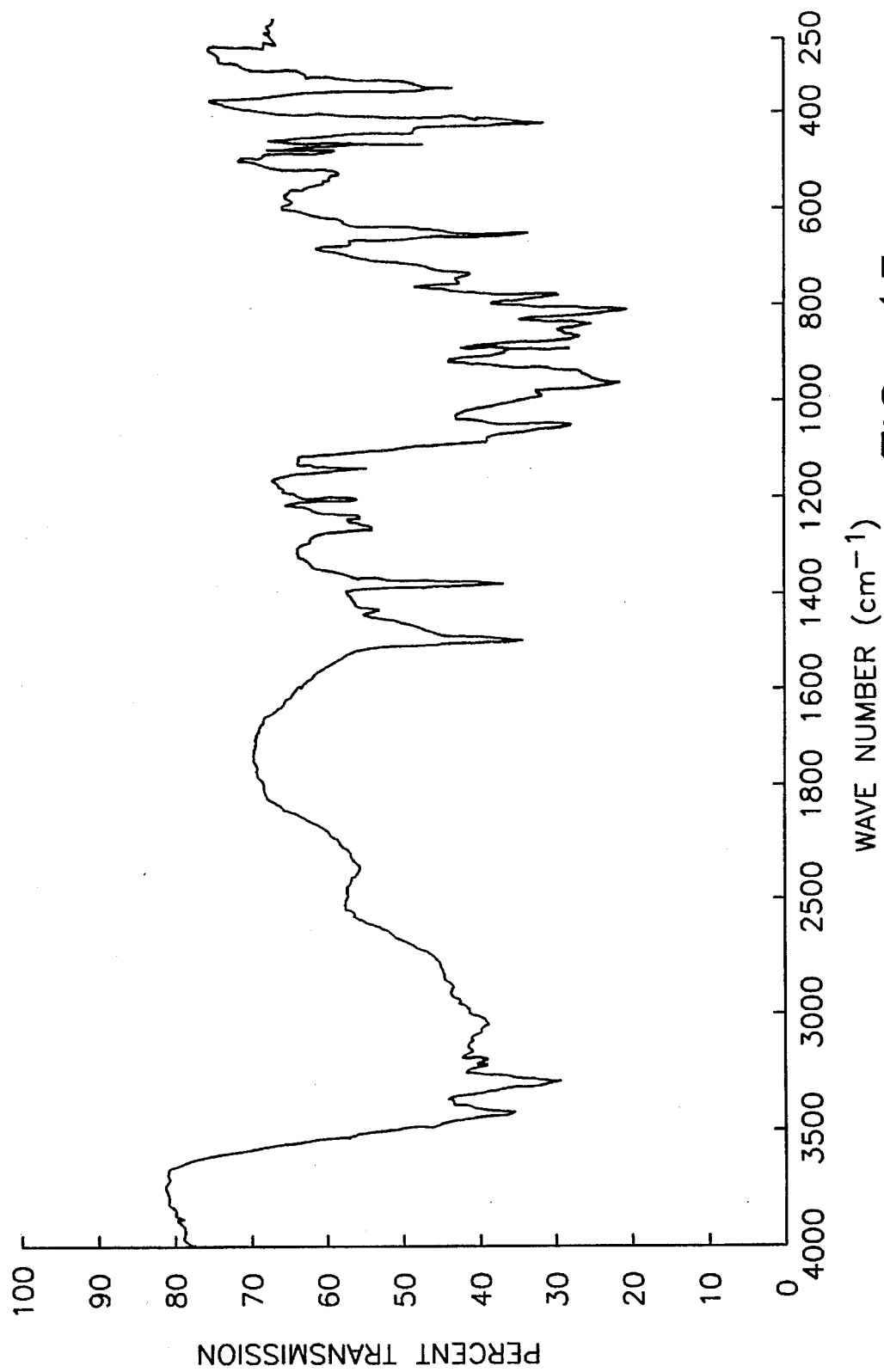

| | Data on crystal forms | | | | | | | | | |
|---|---|---|---|---|---|---|---|---|---|---|
| Crystal code | A | | B | | C | | D | | E | |
| | FIG. 1 | | FIG. 2 | | FIG. 3 | | FIG. 4 | | FIG. 5 | |
| Powder X-ray diffraction | lattice spacing (Å) | relative intensity | lattice spacing (Å) | relative intensity | lattice spacing (Å) | relative intensity | lattice spacin (Å) | relative intensity | lattice spacing (Å) | relative intensity |
| | 13.06 | 19 | 13.06 | 25 | 8.67 | 66 | 8.70 | 35 | 8.84 | 19 |
| | 11.56 | 17 | 9.21 | 22 | 6.81 | 65 | 6.46 | 57 | 6.53 | 42 |
| | 9.15 | 18 | 6.52 | 72 | 5.70 | 98 | 5.71 | 34 | 5.75 | 34 |
| | 6.51 | 67 | 6.50 | 64 | 5.13 | 50 | 5.45 | 100 | 5.51 | 95 |
| | 6.08 | 20 | 4.95 | 17 | 4.41 | 25 | 5.19 | 29 | 5.23 | 29 |
| | 5.81 | 21 | 4.90 | 28 | 4.32 | 49 | 4.84 | 32 | 4.88 | 29 |
| | 4.90 | 44 | 4.81 | 11 | 4.17 | 58 | 4.71 | 87 | 4.75 | 100 |
| | 4.81 | 17 | 4.60 | 10 | 4.02 | 43 | 4.40 | 57 | 4.44 | 49 |
| | 4.50 | 21 | 4.33 | 10 | 3.81 | 48 | 4.35 | 45 | 4.38 | 30 |
| | 4.38 | 100 | 4.27 | 100 | 3.50 | 100 | 3.38 | 80 | 3.39 | 52 |
| | 3.15 | 15 | 3.24 | 9 | 3.38 | 30 | 3.22 | 86 | 3.24 | 91 |
| | 3.01 | 17 | 3.15 | 21 | 3.12 | 34 | 3.18 | 33 | 3.20 | 26 |
| TG-DSC dehydration peak temp. (°C.) | FIG. 6 96 130 147 | | FIG. 7 114 128 156 | | no endothermic peak based on dehydration is detectable | | FIG. 9 142 | | FIG. 10 166 | |
| Infrared | FIG. 11 | | FIG. 12 | | FIG. 13 | | FIG. 14 | | FIG. 15 | |

TABLE 4-continued

| | Data on crystal forms | | | | |
|---|---|---|---|---|---|
| Crystal code | A | B | C | D | E |
| absorption spectrum | | | | | |

REFERENCE EXAMPLE 4

Production Example of Crystal F

Crystal D was dried at 150° C. for 3 hours to obtain anhydride crystal from which 1 mole of water of crystallization had been released.

Figure 16:
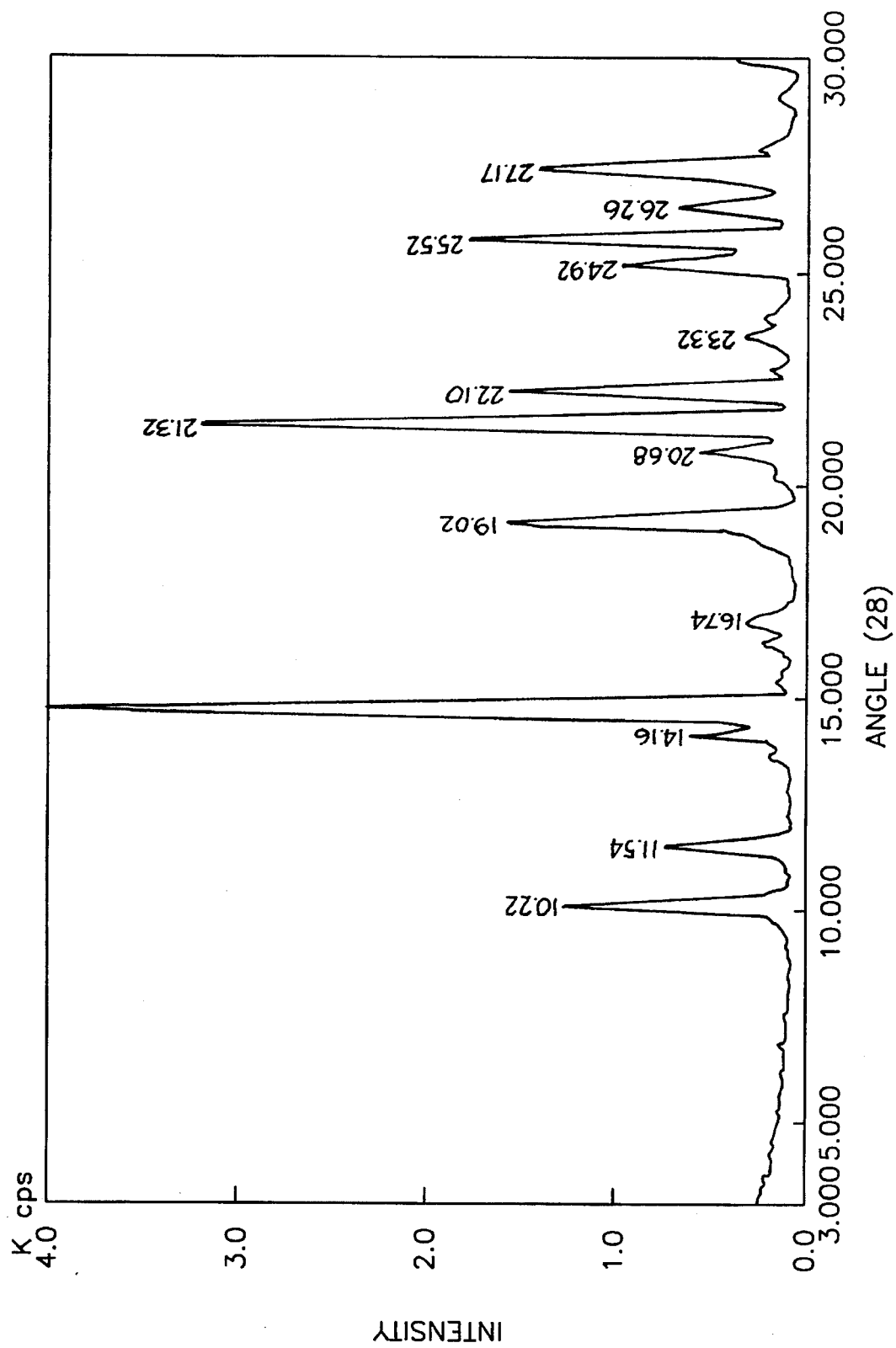
FIG. 16 shows a powder X-ray diffraction spectrum of crystal F, FIGS. 17 to 19 respectively show polarization microphotographs of crystals C, D and E.

Powder X-ray diffraction spectrum of this crystal is shown in FIG. 16. Conditions for the measurement of the powder X-ray diffraction are the same as those described in the foregoing.

Lattice spacing and relative intensity obtained from the powder X-ray diffraction data are shown in Table 5.

TABLE 5

| Lattice spacing and relative intensity | |
|---|---|
| Lattice spacing (Å) | Relative intensity |
| 8.64 | 30 |
| 7.66 | 18 |
| 6.25 | 15 |
| 5.99 | 100 |
| 4.66 | 38 |
| 4.29 | 13 |
| 4.16 | 75 |
| 4.02 | 37 |
| 3.57 | 23 |
| 3.49 | 43 |
| 3.39 | 17 |
| 3.29 | 34 |

As is evident from the results, crystal D has a clearly different pattern in comparison with FIG. 4, and its water can be regarded as water of crystallization.

Example 3

Production Example of Tablets

A 40 g portion of the crystal D of compound (I) was uniformly mixed with 336.8 g of lactose and 84 g of corn starch. A 144 g portion of 10% hydroxypropylcellulose aqueous solution was sprayed on the thus prepared mixture to make it into granules which were subsequently sieved and dried. The thus obtained granules were uniformly mixed with 4.8 g of magnesium stearate, and the mixture was tabletted using a 7.0 m/m 8.4 R punch, thereby obtaining 4,000 tablets each weighing 120.0 mg and containing 10.0 mg of compound (I).

INDUSTRIAL APPLICABILITY

Utility of the compound (I) monohydrate crystals D and E of the present invention was confirmed by the following tests.

Test Example 1

Stability Test of crystals D and E (1) Samples

Crystal E (Lot No. T-4) dehydration peak: 166° C.
Crystal D (Lot No. H-1) dehydration peak: 143° C.

(2) Preservation

Temperature conditions were examined by preserving each sample in a brown bottle sealed up with a screw cap, or without the cap for an open preservation test. Also, each sample was preserved in a weighing bottle for the examination of humidity conditions, or in a colorless Petri dish sealed with a tape for light condition examination.

(3) Test methods

1) Water content

About 100 mg of each sample was weighed precisely and heated at 160° C. for 10 minutes at a nitrogen flow rate of 200 ml/min using a water vaporization apparatus, and the water content was measured by the Karl Fischer's method. A water vaporization apparatus, model VA-05, and an automatic water content measuring apparatus, model KF-05, both manufactured by Mitsubishi Kasei, were used in this test.

2) HPLC area percentage

HPLC area percentage was measured by weighing about 5 mg of each sample, filling up the sample to 10 ml with a mobile phase and injecting a 10 μl portion of the mixture.

Operation conditions

Detector: ultraviolet absorption spectrophotometer (measuring wavelength: 226 nm)

Column: a stainless steel tube of about 4.6 mm in inside diameter and about 15 cm in length, packed with μm of an octadecylsilylated silica gel (Develosil ODS-5)

Column temperature: constant temperature at around room temperature

Mobile phase: mixed solution of 0.01M sodium pyrophosphate containing 1 mM tetrabutylammonium phosphate, adjusted to pH 7.6 with phosphoric acid, and methanol (95:5)

Flow rate: controlled at such a rate that retention time of compound (I) became about 8 minutes The apparatus used was LC-9A manufactured by Shimadzu, and CR4AX manutactured by Shimadzu was used for the data transaction.

3) Quantitative value

About 50 mg of each crystal of compound (I) is weighed precisely and dissolved in 3 ml of N/10 sodium hydroxide solution and water, and the volume is precisely adjusted to 50 ml. A 1 ml portion of the thus prepared solution is measured precisely and mixed with water to adjust the volume precisely to 10 ml. A 1 ml portion of the resulting solution is measured precisely, mixed with 1 ml of an internal standard solution and then the volume is adjusted to 20 ml with a mobile phase, thereby preparing a sample solution. In this instance, bulk material preserved in a refrigerator is treated in the same manner to be used as a standard solution.

A 10 μl portion of each of the sample solution and standard solution is subjected to a liquid chromatography under the following conditions to calculate ratios AT and AS of the peak area of the compound (I) to the peak area of the internal standard substance.

Compound (I) (mg)=standard substance (mg)×AT/AS

Internal standard solution: aqueous solution of resorcin (1→2000)

Operation conditions

Detector: ultraviolet absorption spectrophotometer (measuring wavelength: 226 nm)

Column: a stainless steel tube of about 4.6 mm in inside diameter and about 15 cm in length, packed with 5 μm of an octadecylsilylated silica gel (Develosil ODS-5)

Column temperature: constant temperature at around room temperature

Mobile phase: mixed solution of 0.01M sodium pyrophosphate containing 1 mM tetrabutylammonium phosphate, adjusted to pH 7.6 with phosphoric acid, and methanol (95:5)

Flow rate: controlled at such a rate that retention time of compound (I) became about 8 minutes The apparatus used was LC-9A manufactured by Shimadzu, and CR4AX manufactured by Shimadzu was used for the data transaction.

(4) Results

1) Results of the stability test of crystal E are shown in Table 6.

This crystal was stable against temperature and humidity. Also, decrease in its quantitative value under direct sunlight was not observed, though a small amount of decomposed product was detected.

TABLE 6

Crystal E (Lot. T-4)

| Preservation condition (1 month) | Appearance | Water content | HPLC Area percentage | HPLC Quantitative value |
|---|---|---|---|---|
| 4° C., sealed | reddish white | 5.42% | 99.22% | standard |
| room temp. | | | | |
| sealed | no change | 5.34 | 99.25 | 101.4% |
| open | " | 5.47 | 99.28 | 100.4 |
| 40° C., open | no change | 5.39 | 99.20 | 98.8 |
| 40° C., 75% RH | " | 5.41 | 99.21 | 99.1 |
| 60° C., sealed | no change | 5.32 | 99.25 | 100.3 |
| sunlight | no change | 5.24 | 98.74 | 97.3 |

2) Results of the stability test of crystal D are shown in Table 7.

This crystal was stable under temperature and humidity conditions with no changes in appearance and no decrease in quantitative value.

Also, it was stable when preserved under direct sunlight, though its appearance changed to slightly yellowish color and a small amount of decomposed product was detected on HPLC after 3 months of the preservation.

TABLE 7

Crystal D (Lot. H-1)

| Temp. | Preservation condition | (month) | Appearence | Water content | HPLC Area precent | HPLC Quantivative value |
|---|---|---|---|---|---|---|
| 4° C. | sealed | 1 | Reddish white | 5.58% | 99.92% | standard |
| | | 2 | " | 5.61 | 99.78 | standard |
| | | 3 | " | 5.59 | 99.72 | standard |
| RT | sealed | 1 | No change | 5.50 | 99.91 | 98.8% |
| | | 2 | " | 5.60 | 99.83 | 101.1 |
| | | 3 | " | 5.65 | 99.73 | 99.7 |
| | 75% RH | 1 | No change | 5.46 | 99.94 | 99.4 |
| | | 2 | " | 5.55 | 99.76 | 100.8 |
| | | 3 | " | 5.63 | 99.72 | 99.8 |
| 40° C. | sealed | 1 | No change | 5.64 | 99.93 | 100.4 |
| | | 2 | " | 5.59 | 99.74 | 101.5 |
| | | 3 | " | 5.50 | 99.78 | 100.1 |
| | 75% RH | 1 | No change | 5.56 | 99.91 | 98.0 |
| | | 2 | " | 5.44 | 99.75 | 102.7 |
| | | 3 | " | 5.36 | 99.82 | 100.3 |
| 50° C. | sealed | 1 | No change | 5.55 | 99.94 | 99.2 |
| | | 2 | " | 5.54 | 99.74 | 101.1 |
| | | 3 | " | 5.56 | 99.74 | 99.3 |
| | open | 1 | No change | 5.63 | 99.91 | 99.6 |
| | | 2 | " | 5.63 | 99.74 | 100.7 |
| | | 3 | " | 5.54 | 99.69 | 100.5 |
| 60° C. | sealed | 1 | No change | 5.46 | 99.90 | 100.3 |
| | | 2 | " | 5.68 | 99.78 | 101.6 |
| | | 3 | " | 5.60 | 99.75 | 100.3 |

TABLE 7-continued

Crystal D (Lot. H-1)

| Temp. | Preservation condition (month) | | Appearence | Water content | HPLC Area precent | Quantivative value |
|---|---|---|---|---|---|---|
| open | | 1 | No change | 5.48 | 99.90 | 99.0 |
| | | 2 | " | 5.64 | 99.75 | 101.5 |
| | | 3 | " | 5.58 | 99.73 | 100.7 |
| sunlight | | 1 | Yellowish white | 5.52 | 99.68 | 99.3 |
| | | 2 | Yellowish white | 5.30 | 99.15 | 99.2 |
| | | 3 | Yellowish white | 5.23 | 98.80 | 96.8 |

Test Example 2

Stability test of solid pharmaceutical preparation containing crystal D

The general tablets prepared in Example 3, each of which containing 10 mg of the crystal D of compound (I), were preserved for 1, 3 and 6 months to measure residual ratio of the compound (I) and hardness (kg) of the general tablets, with the results shown in Table 8.

TABLE 8

Stability of general 10 mg tablet

| | Preservation condition | Appearance | Residual ratio (%) | Hardness (kg) |
|---|---|---|---|---|
| Initial | — | white tablet | 100.0 | 5.3 |
| One month | 5°, sealed | no change | 100.0 | 5.0 |
| | 40°, 75% RH, open | no change | 99.9 | 3.4 |
| | 50°, open | no change | 100.1 | 5.1 |
| | light, 1000 Lux | no change | 100.3 | 5.6 |
| Three months | 5°, sealed | no change | 100.0 | 5.8 |
| | 40°, 75% RH, open | no change | 100.0 | 4.4 |
| | 50°, open | no change | 100.5 | 6.2 |
| | light, 1000 Lux | no change | 99.8 | 6.9 |
| Six months | 5°, sealed | no change | 100.8 | 4.4 |
| | 40°, 75% RH, open | no change | 10.9 | 3.1 |
| | 50°, open | no change | 101.2 | 5.7 |
| | light, 1000 Lux | no change | 99.8 | 5.4 |

Test Example 3

Physical stability test of crystal C suspended in water

Sample

Crystal C (Lot No. 49-1) was used.

Test Method

About 100 mg of crystal C was added to 10 ml of water, stirred on a stirrer for predetermined periods (2, 3, 5 and 15 hours) and then dried for 4 hours at room temperature under a reduced pressure (phosphorus pentaoxide).

Test Results

Figure 20:
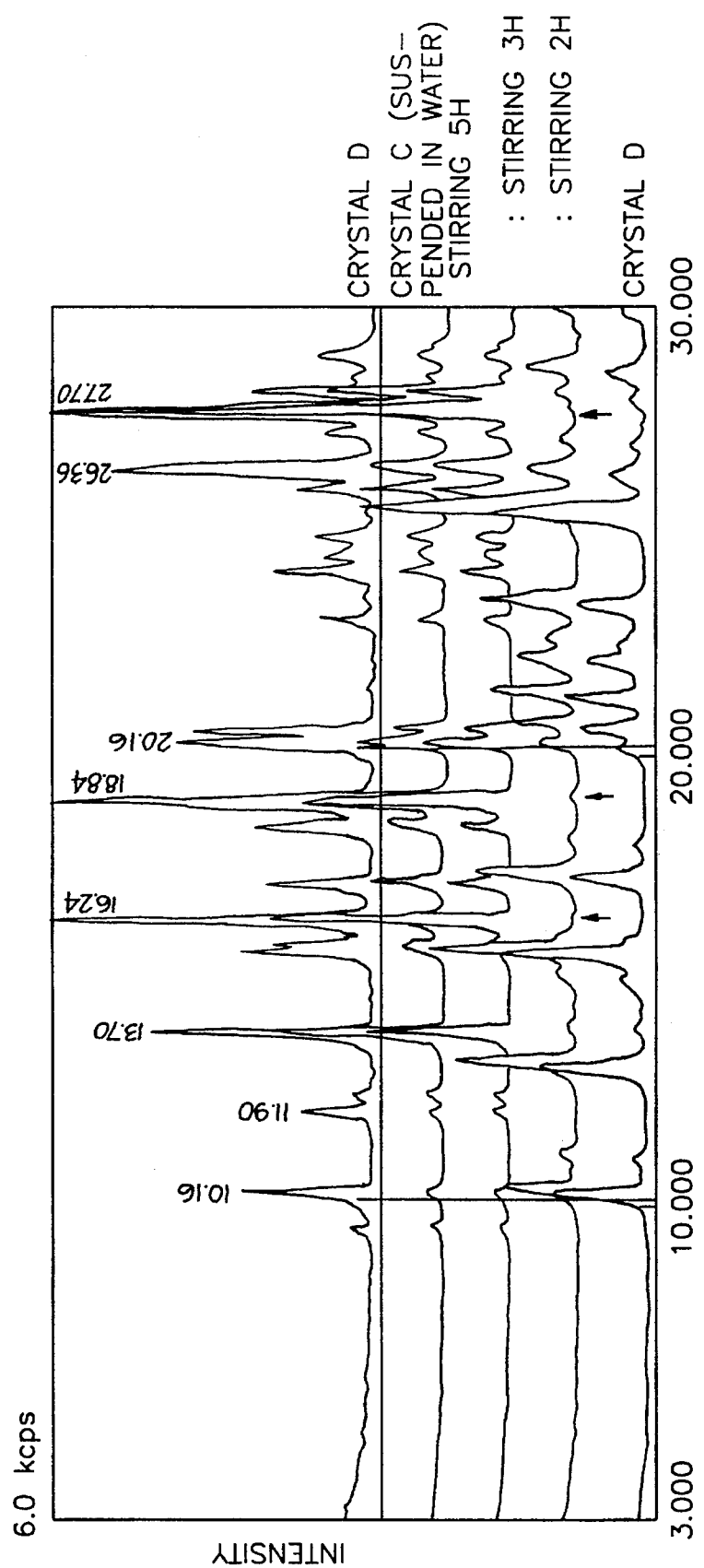
FIG. 20 is a powder X-ray diffraction spectrum showing conversion of crystal C into crystal D under suspended condition in water and FIGS. 21, 22 and 23 respectively show charts of the TG-DSC thermogravimetric analysis of crystal C after 2, 3 and 5 hours of its suspension in water.
Figure 21:
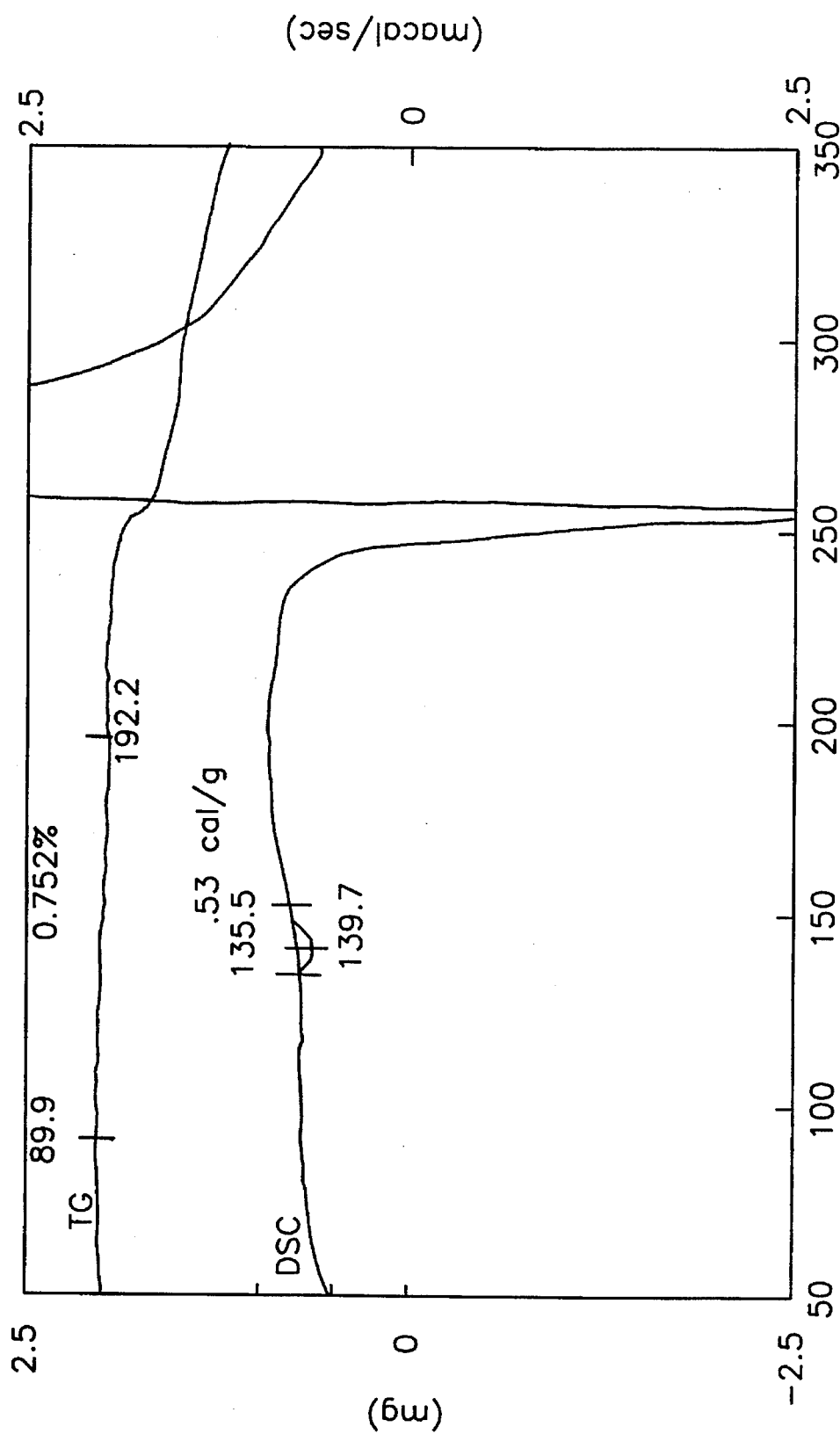
Figure 22:
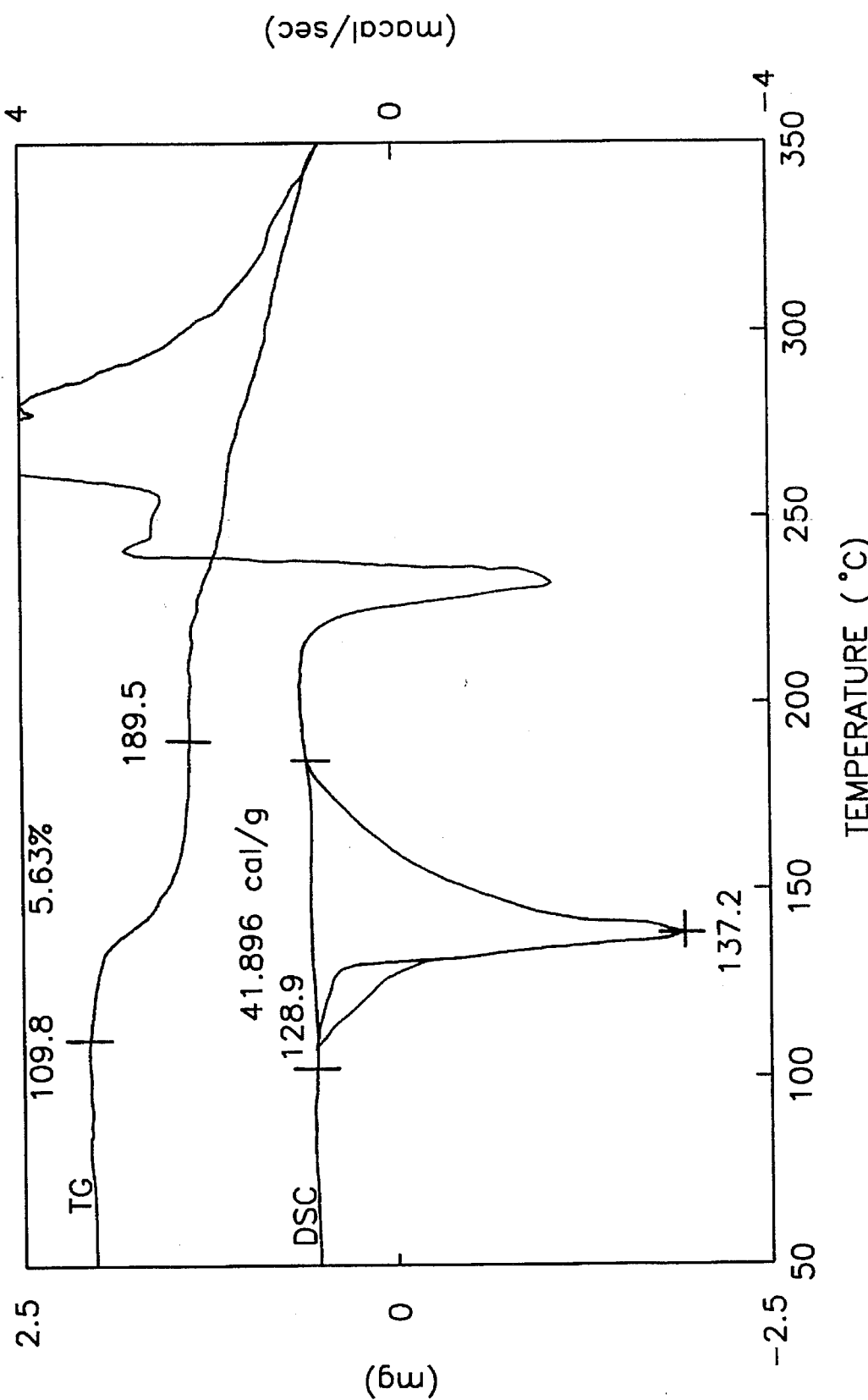
Figure 23:
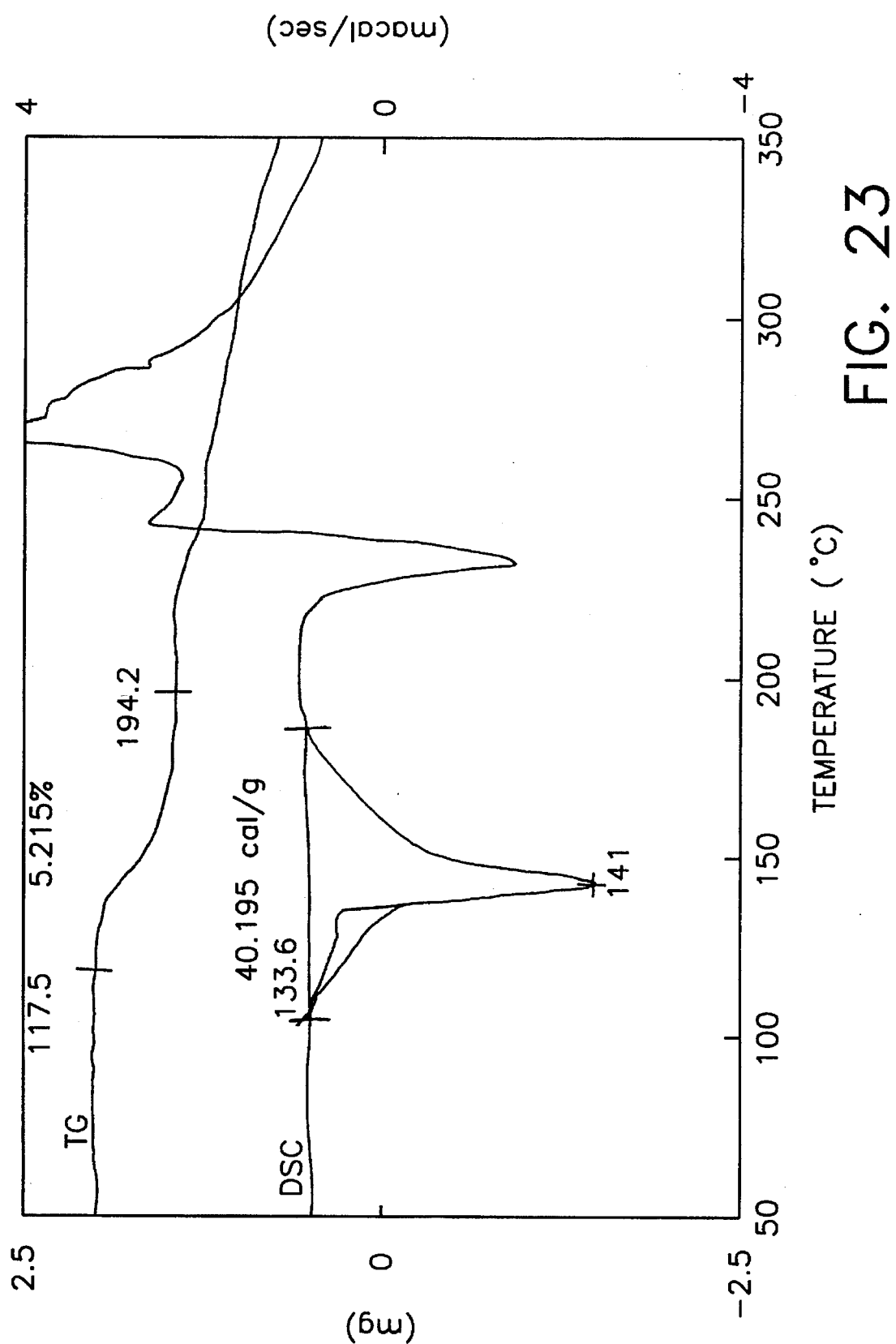

Two hours after suspending the crystal (cf. FIG. 20), a slight pattern of hydrate was observed (a part pointed with an arrow in FIG. 20) and a slight endothermic peak with a weight loss was observed at 139° C. by the thermogravimetric analysis (cf. FIG. 21). As the stirring was continued further, the powder X-ray. diffraction pattern coincided with that of crystal D (Lot No. H-1) (cf. FIG. 20) and an endothermic peak with a weight loss of about 1 mole equivalent was observed at 137° to 143° C. by the thermogravimetric analysis (cf. FIGS. 22 and 23). It was confirmed that the crystalline form of crystal C is physically unstable, because the crystalline form is changed and converted into monohydrate crystal (crystal D) when suspended in water. The results are shown in Table 9.

TABLE 9

Stability of crystal C when suspended in water

| Stirring time | Powder X-ray diffraction | Thermogravimetric analysis (endothermic peak temp. TG weight loss) | |
|---|---|---|---|
| 2 hours | crystal C + D (trace) | 139.7° C. | 0.75% |
| 3 hours | crystal D | 137.2° C. | 5.36% |
| 5 hours | crystal D | 141.° C. | 5.21% |
| 15 hours | crystal D | 143.8° C. | 4.87% |

As is evident also from the above results, the known crystal C causes serious problems during the production and preservation of a solid pharmaceutical preparation of compound (I) because of the hygroscopic property of the crystal and its physical instability in the presence of water, while each of the novel crystals D and E of monohydrate of compound (I) of the present invention is unexpectedly stable in water-suspended condition due to its little hygroscopicity and extremely stable against light and shows sufficient stability even after its storage under a severe high temperature condition of, for example, 3 months at 60° C., hardly causing dehydration and decomposition. In addition, a solid pharmaceutical preparation produced using the inventive crystal does not cause decomposition of the active ingredient even under a severe high temperature test condition of, for example, 6 months at 50° C. and is extremely stable against light and also sufficiently stable in terms of its hardness because the hardness value does not deviate from the practical range.

In addition, because of its production characteristics, crystal D is especially useful for the practical pharmaceutical preparation which must be produced in a large scale.

In consequence, the novel monohydrate crystal D or E of the present invention, especially crystal D, and a solid pharmaceutical preparation using the same exhibit industrially significant effects, because they render possible for the first time practical use as a stable solid pharmaceutical preparation of compound (I) which has bone resorption inhibitory effect, anti-inflammatory effect and analgesic-antipyretic effect and has an excellent drug efficacy for diseases in which increased bone resorption participates.

We claim:

1. A crystal selected from the group consisting of crystals D and E of 1-hydroxy-2-(imidazo[1,2-a]pyridin-3-yl)ethane-1,1-bis(phosphonic acid) monohydrate having the following physicochemical properties (1) crystal D: has the lattice spacing and relative intensity shown in Table 1 in the powder X-ray diffraction spectrum obtained by using Cu-Kα ray and a dehydration peak temperature of 135° to 149° C. according to TG-DSC thermogravimetric analysis

TABLE 1

| Lattice spacing (Å) | Relative intensity |
|---|---|
| 8.77 ± 0.10 | medium |
| 6.50 ± 0.05 | " |
| 5.73 ± 0.03 | " |
| 5.48 ± 0.04 | strong |
| 5.21 ± 0.03 | medium |
| 4.86 ± 0.03 | " |
| 4.73 ± 0.03 | strong |
| 4.42 ± 0.03 | medium |
| 4.37 ± 0.03 | " |
| 3.38 ± 0.02 | slightly strong |
| 3.23 ± 0.02 | strong |
| 3.19 ± 0.02 | medium |

(2) Crystal E: has the lattice spacing and relative intensity shown in the above Table 1 in the powder X-ray diffraction spectrum obtained by using Cu-Kα ray and a dehydration peak temperature of 160° to 170° C. according to TG-DSC thermogravimetric analysis.

2. A crystal of claim 1, which is crystal D of the 1-hydroxy- 2-(imidazo[1,2-a]pyridin-3-yl)ethane-1,1-bis(phosphonic acid) monohydrate.

3. A crystal of claim 1, which is crystal E of the 1-hydroxy- 2-(imidazo[1,2-a]pyridin-3-yl)ethane-1,1-bis(phosphonic acid) monohydrate.

4. A solid pharmaceutical preparation which comprises a crystal selected from the group consisting of crystals D and E of the 1-hydroxy-2-(imidazo[1,2-a]pyridin-3-yl)ethane-1,1-bis(phosphonic acid) monohydrate of claim 1 and a carrier for solid pharmaceutical preparation use.

5. The solid pharmaceutical preparation according to claim 4, wherein said solid pharmaceutical preparation contains crystal D of the 1-hydroxy-2-(imidazo[1,2-a]pyridin-3-yl)ethane-1,1-bis(phosphonic acid) monohydrate.

6. The solid pharmaceutical preparation according to claim 4, which is a preparation for preventing and/or treating diseases in which increased bone resorption participates.

7. The solid pharmaceutical preparation according to claim 6, which is a preparation for preventing and/or treating osteoporosis.

8. A method for treating osteoporosis in a host inflicted with such a condition which comprises administering to said host, an osteoporosis inhibiting amount of the pharmaceutical preparation of claim 4.

9. A method for treating osteoporosis in a host inflicted with such a condition which comprises administering to said host, an osteoporosis inhibiting amount of the pharmaceutical preparation of claim 5.

* * * * *